United States Patent [19]

Itazaki et al.

[11] Patent Number: 4,595,767

[45] Date of Patent: Jun. 17, 1986

[54] 1,4-BENZODIOXINE AND 1,4-BENZODIOXINE DERIVATIVES AND PRODUCTION THEREOF

[75] Inventors: Hiroshi Itazaki, Hyogo; Kunio Hayashi; Munenori Matsuura, both of Osaka; Yukio Yonetani, Nara; Masuhisa Nakamura, Osaka, all of Japan

[73] Assignee: Shionogi & Co., Ltd., Osaka, Japan

[21] Appl. No.: 791,160

[22] Filed: Oct. 22, 1985

[30] Foreign Application Priority Data

Nov. 14, 1984 [JP]  Japan ................................ 59-241506

[51] Int. Cl.[4] ................. C07D 409/00; C07D 319/14; A61K 31/38
[52] U.S. Cl. ....................................... 549/60; 549/362
[58] Field of Search ................................ 549/60, 362

[56] References Cited

U.S. PATENT DOCUMENTS

| 4,097,582 | 6/1978 | Briet et al. | 549/60 |
| 4,177,286 | 12/1979 | Doria et al. | 549/60 |
| 4,205,076 | 5/1980 | Durham et al. | 549/362 |
| 4,517,184 | 5/1985 | Habicht et al. | 549/60 |
| 4,545,993 | 10/1985 | Okamoto et al. | 549/60 |

FOREIGN PATENT DOCUMENTS 3329126  2/1985  Fed. Rep. of Germany ...... 549/362

*Primary Examiner*—Alan Siegel
*Attorney, Agent, or Firm*—Wenderoth, Lind & Ponack

[57] ABSTRACT

Highly safe new diuretics, i.e., 1,4-benzodioxane and 1,4-benzodioxine derivatives having potent antihypertensive activity but no or little uricesuric activity, which can be administered to human orally, intravenously, or hypodermically at a respective daily dosage of 0.1–2 mg/kg, 0.005–0.1 mg/kg, or 0.02–0.4 mg/kg.

2 Claims, No Drawings

4,595,767

1,4-BENZODIOXANE AND 1,4-BENZODIOXINE DERIVATIVES AND PRODUCTION THEREOF

BACKGROUND OF THE INVENTION

1. Field of the Invention

The present invention provides novel compounds having diuretic with antihypertensive activities. More particularly, it relates to 1,4-benzodioxane or 1,4-benzodioxine derivatives and processes for the production thereof.

2. Prior Art 1,4-Benzodioxane compounds have long been studied, for instance, it has been disclosed in Journal of Medicinal Chemistry 8, 446 (1965) that 2-guanidinomethyl-1,4-benzodioxane demonstrates antihypertensive action and adrenergic blocking action. The present inventors synthesized 1,4-benzodioxanesulfonamide derivatives having antihypertensive action which have been disclosed in JPN Unexam. Pat. Pub. No. 55-124781.

SUMMARY OF THE INVENTION

This invention relates to a series of novel 1,4-benzodioxane and 1,4-benzodioxine derivatives and a process for production thereof, having an excellent diuretic and antihypertensive activity but have no or little uricosuric activity, more particularly, it relates to compounds of the formula:

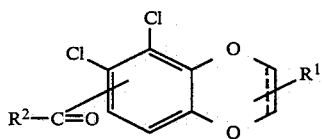

wherein $R^1$ is optionally protected hydroxymethyl or carboxy; $R^2$ is hydrogen, straight or branched chain lower alkyl or lower alkenyl, $C_4$–$C_7$ cycloalkyl, optionally substituted pheny, phenyl(lower alkyl), hydroxy, thienyl, or furyl; and the dotted line indicates the presence or absence of a double bond and processes for production of compounds represented by the above-shown formula (I), which is characterized by reaction of 3,4-dichloro-1,2-benzenediol of the formula:

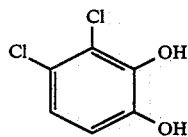

with α-epihalohydrin or the equivalent reagent thereof in the presence of a base followed by acylation in the presence of Lewis acid; or characterized by acylation of 3,4-dichloro-1,2-benzenediol in the presence of Lewis acid followed by reaction with α-epihalohydrin or the equivalent reagent thereof in the presence of a base, and if necessary, subsequent oxidation or dehydrogenation after the oxidation.

DESCRIPTION OF THE PREFERRED EMBODIMENT

Problem to be Resolved

Diuretic thiazides which show a moderate antihypertensive activity or oral administration have been used over many years as first-choice drug. However, it has been a severe defect that they are usually accompanied by uricosuric action. As a result of so many studies for curing said defect, some sorts of phenoxy acetic acid derivatives such as thienylic acid, indacrinone and the like have been developed, but a very few number of the drugs have been marketed. Developement of highly safe drugs are therefore desired.

The present inventors synthesized a series of novel 1,4-benzodioxane and 1,4-benzodioxine derivatives and found that these novel compounds have an excellent diuretic and antihypertensive activity but have no or little uricosuric activity. Consequently the present inventors have accomplished this invention.

Means for Resolving the Problem

The starting materials shown by the formula (II), from which the compounds of this invention can be prepared, are known compounds and disclosed in Biochemical Journal 59, 410 (1955).

In this invention, representatives of the protecting group for the protection of hydroxymethyl or carboxy are for example acyls derived from fatty acids such as acetyl and propionyl as said group for the former; and conventional ester forming groups as said group for the latter, i.e., lower alkyls such as methyl, ethyl and propyl or phenyl optionally substituted by halogen.

Straight or branched chain lower alkyl is $C_1$–$C_4$ alkyl and includes methyl, ethyl, n-propyl, i-propyl, n-butyl, i-butyl, sec-butyl, and t-butyl. Straight or branched chain lower alkenyl is $C_2$–$C_5$ alkenyl and includes for example vinyl, allyl, propenyl, isopropenyl, 1-, 2-, or 3-butenyl, 1-pentenyl, 1-ethylvinyl, and 1-propylvinyl. $C_4$–$C_7$ cycloalkyl includes for example cyclobutyl, cyclopentyl, cyclohexyl, and cycloheptyl. Optionally substituted phenyl is a monocyclic compound which may be substituted by one or two substitutions, e.g., halogen, methyl, and ethyl. Phenyl(lower alkyl) is said lower alkyl substituted by phenyl and includes for example benzyl, phenethyl, and phenylpropyl.

As illustrated by the following reaction scheme, the present compounds (Ia) and (Ib) are readily prepared by the reaction of 3,4-dichloro-1,2-benzenediol with α-epihalohydrine or the equivalents thereof and acylation or by acylation of 3,4-dichloro-1,2-benzenediol and reaction with α-epihalohydrine or the equivalents thereof, if necessary followed by oxidation or dehydrogenation after the oxidation.

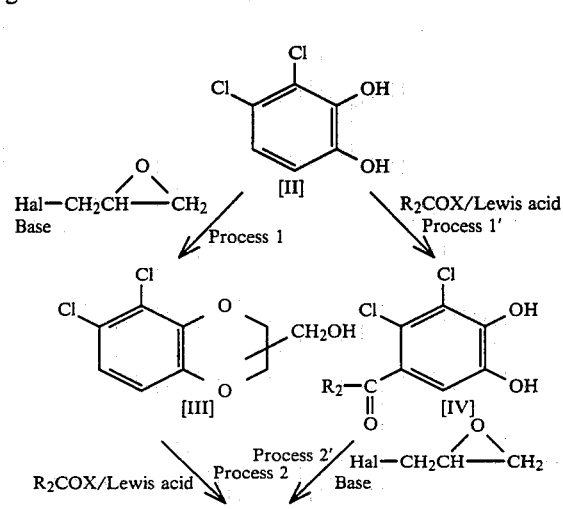

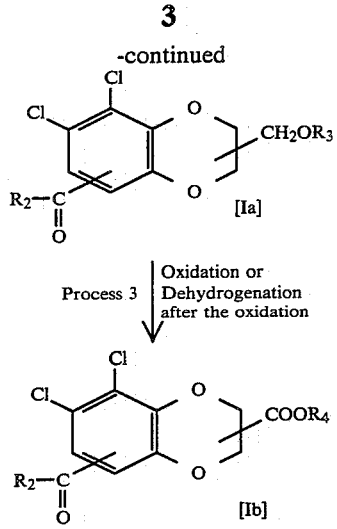

Wherein $R^2$ and the dotted line each has the same meaning as defined above, and $R^3$ and $R^4$ each is hydrogen or a protecting group.

Each step of the processes shown above is explained below.

ROUTE 1

Process 1

The reaction in this process is cycloaddition of the starting material (II) with α-epihalohydrin or the equivalents thereof and carried out in the presence of a base. 2- Or 3-hydroxymethyl compound (Ia) or (Ib) can be obtained selectively by specifying the reaction conditions, e.g., sort of the base and the like.

Method Aa:

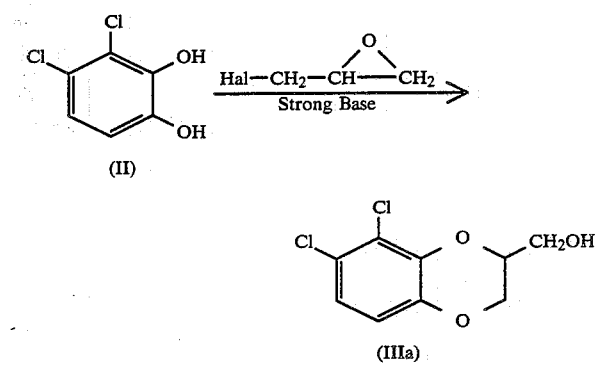

In the reaction for obtaining the compound (IIIa), the starting material is subjected to cycloaddition with an equivalent or slight excess amount of α-epihalohydrin or the equivalents thereof in the presence of a strong base at an amount of about 1.5 to about 3 eq. preferably at about 2 to about 2.3 eq. In this reaction, it should be cautious to choose and fix the sort and the amount of the base employed. If a strong base is employed at an amount below 2 eq. or if the basicity of the base is weak, then the objective compound (IIIa) would be obtained in a lower yield. It is preferable to carry out this reaction at a fairly lower temperature: for instance, the reaction is carried out at 0° C. or under reflux, more preferably at 20° to 30° C. and completed within several minutes to several hours.

α-Epihalohydrin or the equivalents thereof employed in this invention involve epihydrins substituted by halogen or electron-attracting group, wherein chlorine, bromine, and iodine are exemplified as the former and tosyloxy, mesyloxy, and the like are exemplified as the latter.

The strong base employed in this process includes alcoholate such as potassium t-butoxide and sodium t-pentylate; amide such as sodium amide, potassium amide, lithium diethylamide, lithium diisopropylamide, and sodium bis-(trimethylsilyl)amide; and hydride such as sodium hydride and lithium hydride.

The solvent employed may be chosen according to the sort of the base or the solubility of the reactant: for example, alcohols such as t-butyl alcohol, ethers such as tetrahydrofuran (THF) and 1,2-dimethoxyethane, benzene-type solvents such as benzene, toluene, and xylene, and aprotic polar solvents such as dimethylsulfoxide and dimethylformamide (DMF).

Method Ab:

As an alternative process, the 2-hydroxy group of the starting material (II) may be protected by a suitable ethereal group and then subjected to addition of α-epihalohydrin or the equivalents thereof.

In order to introduce said ethereal protecting group selectively at the 2-hydroxy, it is preferable to employ such a base as listed above at an amount over eqivalent, preferably at about 1 to about 1.3 eq. If said base is employed over 2 eq. in this occasion, the protecting group would be introduced at 1-hydroxy.

Any protecting group can be employed as long as they are stable to said base. Benzyl-type protecting groups such as benzyl, benzhydrile, and nitrobenzyl or methoxymethyl is preferable for this process. The reaction may be carried out in a conventional manner for introduction of protecting groups, the solvent for which can also be chosen, as mentioned above, according to the sort of the base and solubility of the reactant.

Thus obtained 2-protected-3,4-dichlorophenol is, in the presence of a base, subjected to addition of α-epihalohydrin or the equivalents thereof, then deprotected in a conventional manner by hydrogenolysis with for example palladium/carbon, and cyclized by the treatment with an alkali.

Method B:

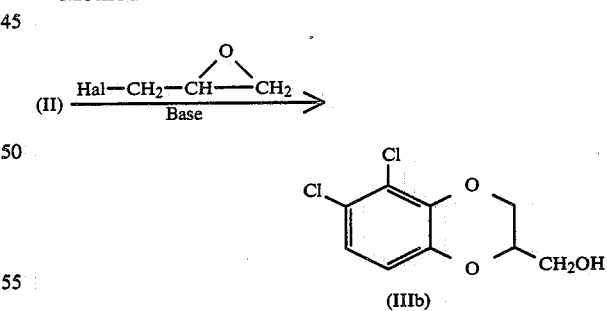

There are two ways for obtaining the compound (IIIb) as mentioned in section (1), i.e., direct cycloaddition of α-epihalohydrin or the equivalents thereof to the starting material or cycloaddition after introduction of a protecting group.

For the way of the direct cycloaddition, the starting material is reacted with α-epihalohydrin or the equivalents thereof in the presence of a weak base. It is preferable to employ said weak base at an equimolar or excess amount, preferably at 3 to 5 moles. Representatives of the weak bases employed are carbonates or hydrogen-carbonates such as potassium carbonate and sodium carbonate, organic bases such as pyridine and triethylamine, or the like. The solvent employed may be chosen according to the sort of the base or the solubility of the reactant therein: for example, ketones or esters such as acetone and ethyl acetate and hydrophilic solvents like alcohols such as methanol, ethanol, and isopropanol.

For the way of cycloaddition subsequent to introduction of a protecting group, the starting material (II) is protected at the 1-hydroxy by a suitable ethereal protecting group and then reacted with α-epihalohydrin or the equivalents thereof for cycloaddition. The introduction of the protecting group may be carried out in a conventional manner as explained in (1), but the sort and the amount of the base should be carefully selected and fixed. In order to introduce said ethereal protecting group selectively at the 1-hydroxy, the reaction should be carried out by using the strong base as exemplified in (1) at an amount of 2 moles or more, preferably at about 2 to about 2.3 moles.

Any protecting group stable to bases may be employed for this process and the protecting groups listed in (1) are the examples. Solvents exemplified in (1) may be also employed according to the sort of the bases or solubility of the reactants. After the introduction of the protecting group, addition of α-epihalohydrin or the equivalents thereof, deprotection by hydrogenation or the like, and then cyclization by treatment with alkali are carried out: theses reactions may be carried out accroding to the manners shown in (1).

Process 2

In this process, an acyl is introduced to the benzene nucleus of a 2- or 3-hydroxymethyl compound (IIIa or IIIb) obtained in Process 1 to give a compound (Ia). This process may preferably be carried out after the protection of hydroxy of the compound (III) by a protecting group stable to acids. If desired, the compounds (Ib) may be prepared by a conventional oxidation of the compound (IIIa) or (IIIb) as the corresponding carboxylic acid, or by further esterification and introduction of an acyl.

The introduction of acyls in this process may be carried out in a conventional manner, for example, by the Friedel Crafts reaction. This reaction is carried out in the presence of a Lewis acid such as alminium chloride, zinc chloride, ferric chloride or titanium tetrachloride, wherein an acyl halide or acid anhydride having a group to be introduced as an acylating agent may be employed and chlorine, bromine, and iodine as halogen of acyl halide are exemplified.

Solvents may be chosen from usual solvents employed in the Friedel Crafts reaction according to the sort of acid catalysts or solubility of the reactants: for example, hydrocarbon-type solvent such as dichloromethane, dichloroethane and carbon tetrachloride, cyclohexane, carbon disulfide, nitromethane or the like may be employed.

The protected- or acyl-ester compounds obtained by the Friedel Crafts reaction may be, if desired, converted to the free alcohols by alkali hydrolysis.

Process 3

This process is characterized by the oxidation of a 2- or 3-hydroxymethyl compound (Ia) to give the carboxylic acid or the ester (Ib) and the subsequent dehydrogenation to give the corresponding carboxylic acid of dioxine-form or the ester (Ib).

All of usual oxidation reactions converting a primary or a secondary alcohol into the carboxylic acid or the ketone may be employed as long as they are carried out under such conditions as to avoid side-reactions at other functional groups. For instance, the Jones Oxidation method disclosed in *Journal of Chemical Society* 39 (1946), i.e., chromic acid oxidation with Jones' reagents in acetone is recommended.

The products after the oxidation may, if desired, be converted to 1,4-benzodioxine compounds (Ib) by dehydrogenation.

Reactions with N-bromosuccinimide (NBS) are examples of said dehydrogenation. The reaction is carried out, by refluxing under anhydrous conditions, in carbon tetrachloride using benzoyl peroxide as a reaction initiator and it is completed within a period of several hours or several days.

ROUTE 2

In this Route, Process 1 and Process 2 follow the reverse course of those employed in Route 1. As shown in the foregoing reaction scheme, 3,4-dichloro-1,2-benzenediol (II) is acylated by the Friedel Crafts reaction (Process 1') and then applied to cycloaddition (Process 2') with α-epihalohydrin or the equivalent reagent thereof to yield the compounds (Ia). In this route, 6-acyl-1,4-dioxane or 6-acyl-1,4-dioxine derivatives are obtained.

Process 1'

This process may be carried out according to the Friedel Crafts reaction employed in Process 2 of Route 1. The reaction conditions, i.e., the solvents employed, the reagents, and the like may also be determined according to the disclosure in Process 2 of Route 1.

Acyl group is introduced selectively at 5-position of the compound (II) and rarely at the 6-position. Since the acyl group is also reacted with 1- and 2-hydroxy groups to form an ester, it is necessary to convert the ester to the free alcohol by alkali hydrolysis for the subsequent process.

Process 2': Method A

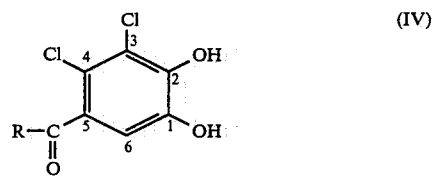

In this process, the optionally protected 2-hydroxymethyl compounds (Ia-a) are prepared by cycloaddition of α-epihalohydrin or the equivalent reagent thereof to 5-acyl-3,4-dichloro-1,2-benzenediol (IV).

The process may be carried out according to Method A of Process 1 in said route 1. The objective 2-hydroxymethyl compounds (Ia-a) can be obtained under the condition, i.e., the sort and amount of the base employed, the reaction temperature, the reaction time, and the like, fixed according to the Method A of Process 1.

α-Epihalohydrin or the equivalent reagent thereof may be subjected to cycloaddition directly or subsequently to protection of 2-hydroxy or the compounds (IV) by a suitable protecting group.

Solvents employed may be chosen from the examples disclosed in Process 1 in consideration of the solubility of the reactant.

Process 2': Method B

In this process, the optionally protected 3-hydroxymethyl compounds (Ia-b) are prepared by cycloaddition of α-epihalohydrin or the equivalent reagent thereof to the compounds (IV) obtained in Process 1'.

The objective compounds (Ia-b) can be obtained by the Method B of Process 1 by properly choosing the sort or amount of the base employed and conditions of the reaction temperature, the reaction time, and the like.

α-Epihalohydrin or the equivalent reagent thereof may also be subjected to cycloaddition directly or subsequently to protection of the 1-hydroxy of the compounds (IV) by a suitable protecting group.

The compounds (Ia) thus obtained through Route 2 may be, if desired, employed for the next 3rd process to obtain the compounds (Ib).

In this process, if $R^2$ is a lower alkenyl, the Friedel Crafts reaction using acylating agent $R^2COX$ wherein $R^2$ is a lower alkenyl can be applied and particularly if the functional group adjacent to carbonyl of $R^2CO-$ is for example an activated methylene $-CH_2-$, the reaction with an aldehyde or a ketone to give the alkenyl compound can also be applied (see Example 12).

The present invention is explained in more detail by the following Examples, which do not limit the scope of the present invention.

EXAMPLE 1

Process 1 (Method Aa)

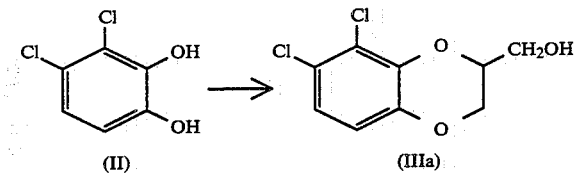

To a solution of 9.04 g of 3,4-dichloro-1,2-benzenediol (II) in 190 ml of dry dimethylformamide (DMF) is added 4.25 g (2.1 equivalent weight) of a 60% sodium hydride oily suspension under cooling on an ice bath (internal temperature 5°–10° C.) and under flowing of nitrogen gas. The temperature of the mixture is raised to room temperature (20°–25° C.), then a solution of 8.30 g (1.2 equivalent) of epibromohydrin in 10 ml of dry DMF is added to the mixture and the resultant mixture is stirred at room temperature (20°–25° C.) for 1 hour. After termination of the reaction, the reaction mixture is poured into about 600 ml of ice-cold water and extracted twice with ether. The ether layer is washed twice with a saturated aqueous solution of sodium chloride, dried over sodium sulfate and evaporated under reduced pressure to give 10.01 g of a residue. The residue is chromatographed on a silica-gel column with dichloromethane, to give 1.60 g of an oily material (oil of sodium hydride) as the first fraction, 1.22 g (Yield 8.3%) of 2-(2,3-epoxypropyloxymethyl)-7,8-dichloro-1,4-benzodioxane as the second fraction, and 6.17 g of 2-hydroxymethyl-7,8-dichloro-1,4-benzodioxane (IIIa) as the last fraction. Yield 52%. The last fraction is recrystallized from hexane-ether to give a pure substance, m.p. 53°–55° C.

Process 1 (Method Ab)

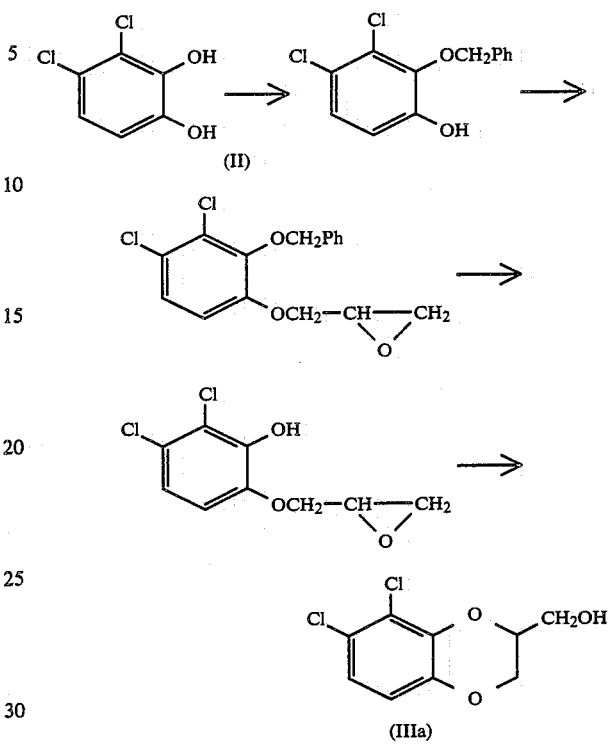

To a solution of 8.95 g (0.05 mole) of the compound (II) dissolved in 300 ml of dry DMF is added a solution of 2.2 g (0.055 mole) of 60% sodium hydride oily suspension and 9.4 g (0.055 mole) of benzyl bromide in 30 ml of DMF. The mixture is stirred at 100° C. for 2 hours, then poured into 400 ml of water and extracted with ether. The ether layer is washed twice with 100 ml of a diluted aqueous solution of sodium hydroxide, washed with water, dried and then evaporated to give 5.9 g of a residue. This is recrystallized from hexane to give 3.79 g of 1,2-dibenzyloxy-3,4-dichlorobenzene. Yield 21.1%, mp. 74°–75.5° C.

Anal. Calcd. (%) for $C_{20}H_{16}O_2Cl_2$ (MW. 359.256): C 66.87, H 4.49, Cl 19.74, Found (%): C 67.49, H 4.75, Cl 19.44.

IR(Nujol) νmax: 1585 cm$^{-1}$.

NMR(CDCl$_3$) δppm: about 7.36(10H), 7.12, 6.78(2×1H, d, 9 Hz) 5.07, 5.04(2×2H, s).

The above sodium hydroxide layer is acidified with hydrochloric acid and extracted with ether. The organic layer is washed with water, dried and evaporated to give 8.37 g of a residue. This is chromatographed on 150 g of silica-gel and eluted with benzene. The eluate is recrystallized from pentane to give 5.464 g of 1-hydroxy-2-benzyloxy-3,4-dichlorobenzene.

Yield 40.6%, mp. 61° C.

Anal. Calcd. (%) for $C_{13}H_{10}O_2Cl_2$ (MW. 269.13): C 58.02, H 3.75, Cl 26.35, Found (%): C 57.32, H 3.82, Cl 26.12.

IR(Nujol) νmax: 3400, 1590, 1570 cm$^{-1}$.

NMR(CDCl$_3$) δppm: about 7.40(5H), 7.12, 6.75(2×1H, d, 9 Hz), 5.41(1H, s), 5.05(2H, s).

To a solution of 2.69 g of 1-hydroxy-2-benzyloxy-3,4-dichlorobenzene dissolved in 100 ml of dry DMF are added 480 mg of 60% sodium hydride oily suspension and 1.685 g of epibromohydrin, and the mixture is stirred at 80° C. for 6 hours. The reaction mixture is poured into 200 ml of water and extracted three times with 200 ml of ether. The organic layer are washed with water, dried and evaporated to give 3.5 g of a residue. This is recrystallized from n-hexane to give 2.569 g of 1-(2,3-epoxypropyloxy)-2-benzyloxy-3,4-dichlorobenzene, yield 79.0%, mp. 65° C.

Anal. Calcd. (%) for $C_{16}H_{14}O_3Cl_2$ (molecular weight 325.194): C 59.10, H 4.34, Cl 21.80, Found (%): C 58.87, H 4.24, Cl 22.06.

IR(Nujol) $\nu$max: 1580 cm$^{-1}$.

NMR(CDCl$_3$) $\delta$ppm: 7.59–7.23(5H), 7.13, 6.78(2×1H, d, J=9 Hz), 5.05(2H, s), 4.33–3.81(2H), about 3.32(1H), 2.90–2.64(2H).

In 140 ml of ethyl acetate, 5.595 g of 1-(2,3-epoxypropyloxy)-2-benzyloxy-3,4-dichlorobenzene is hydrogenated under atmospheric pressure using 1.65 g of 5% palladium on carbon (50% moisture) as catalyst (for 20 minutes, 625 ml of hydrogen gas is absorbed.). After the catalyst is filtered off, the filtrate is evaporated to give 4.3 g of 1-(2,3-epoxypropyloxy)-2-hydroxy-3,4-dichlorobenzene.

NMR(CDCl$_3$) $\delta$ppm: 6.93, 6.74(2×1H, d, J=9 Hz), 4.41–3.91(2H), 3.47–3.30(1H), 3.01–2.79(2H).

To a solution of the product dissolved in 50 ml of ethanol is added 10 ml of 2N sodium hydroxide, and the mixture is heated at 80° C. for 5 minutes, then concentrated to give a residue, to which water is added and extracted with ether. The organic layer is washed with water, dried and evaporated to give 3.16 g of a residue, which is passed through a column of 20 g of silica-gel and eluted with dichloromethane to give 3.104 g of an objective compound, 2-hydroxymethyl-7,8-dichloro-1,4-benzodioxane (IIIa).

Yield 76.7%, mp. 53°–55° C.

Anal. Calcd. (%) for $C_9H_8O_3Cl_2$ (molecular weight 235.068): C 45.99, H 3.43, Cl 30.16, Found (%): C 46.07, H 3.53, Cl 29.53.

IR(CHCl$_3$) $\nu$max: 3580, 3400, 1590, 1570 cm$^{-1}$.

NMR(CDCl$_3$) $\delta$ppm: 6.94, 6.72(2×1H, d, J=9 Hz), 4.38–4.03(3H), 3.96–3.83(2H), 2.13(1H, t, J=6 Hz).

Process 2: Method Aa

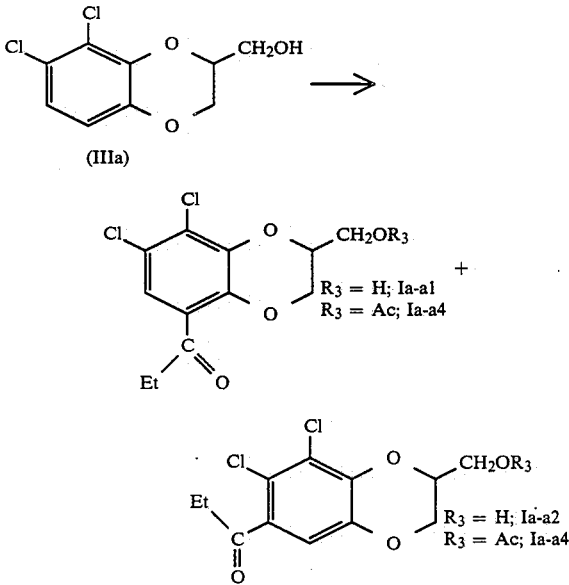

A solution of 4 g of the compound (IIIa), 7.9 g (5 equivalent) of propionyl chloride, and 9.06 g (4 equivalent) of aluminium chloride dissolved in 50 ml of dry dichloromethane is stirred at room temperature for 30 minutes and then refluxed for 2 hours. After cooled, the reaction mixture is poured into a mixture of concentrated hydrochloric acid with ice, and extracted three times with dichloromethane. The organic layer is washed with a saturated aqueous solution of sodium chloride, with 2N sodium hydroxide, and then twice with saturated aqueous solution of sodium chloride, dried over sodium sulfate, and evaporated under reduced pressure to give 6.00 g of a residue. Immediately, this 6.00 g is dissolved in 60 ml of dioxane and 30 ml of 1N sodium hydroxide, and the solution is heated for 5–10 minutes (which becomes a clear solution) and allowed to stand for about an hour. The resulting solution is poured into about 150 ml of water, extracted three times with dichloromethane. The organic layer is washed twice with a saturated aqueous solution of sodium chloride, dried over sodium sulfate and evaporated under reduced pressure to give 5.10 g of a crystalline residue, which is recrystallized from ether to give 1.95 g of 2-hydroxymethyl-5-propionyl-7,8-dichloro-1,4-benzodioxane (Ia-a1), mp. 121°–123° C. The compound (Ia-a1) is further recrystallized from dichloromethane-ether to give 1334 mg of a pure product (Ia-a1), yield 27% [the first crop: 1114 mg (mp. 124°–125° C.) and the second crop: 220 mg (mp. 122°–124° C.)]. Crystalline residue (3580 mg) is recovered from the mother liquor.

In 30 ml of pyridine and 20 ml of acetic anhydride is dissolved 3.58 g of the crystalline residue containing the compound (Ia-a1) and 2-hydroxymethyl-6-propionyl-7,8-dichloro-1,4-benzodioxane (Ia-a2), and the solution is allowed to stand overnight at room temperature to give 2-acetoxymethyl-5-propionyl-7,8-dichloro-1,4-benzodioxane (Ia-a3) and 2-acetoxymethyl-6-propionyl-7,8-dichloro-1,4-benzodioxane (Ia-a4), respectively. After the solvent is removed by evaporation under reduced pressure, the residue is extracted three times with dichloromethane. The organic layer is washed twice with a saturated aqueous solution of sodium chloride, dried over sodium sulfate, and evaporated to give 4.00 g of a residue. The residue is separated into two fractions by using two columns of Lober B (Merck) with hexane:acetone (4:1) as an eluent. The former fraction gives 1380 mg of the compound (Ia-a3), which is recrystallized from ether-hexane to give 1303 mg of the pure product (Ia-a3), yield 23%, mp. 67°–70° C. The latter fraction gives 2180 mg of the compound (Ia-a4), which is recrystallized from ether-hexane to give 2050 mg of the pure product (Ia-a4), yield 36%, mp. 74°–77° C.

A solution of 1305 mg of the compound (Ia-a3) dissolved in 20 ml of dioxane and 10 ml of 1N sodium hydroxide is heated for 5–10 minutes, then allowed to stand at room temperature for 1 hour, poured into water and then extracted three times with dichloromethane. The organic layer is washed twice with a saturated aqueous solution of sodium chloride, dried over sodium sulfate, and evaporated to give 1200 mg of a residue, which is recrystallized from ether-hexane to give 1000 mg of the pure product (Ia-a1), yield 88%, mp. 122°–124° C.

Process 2 (General Procedure for Method Aa)

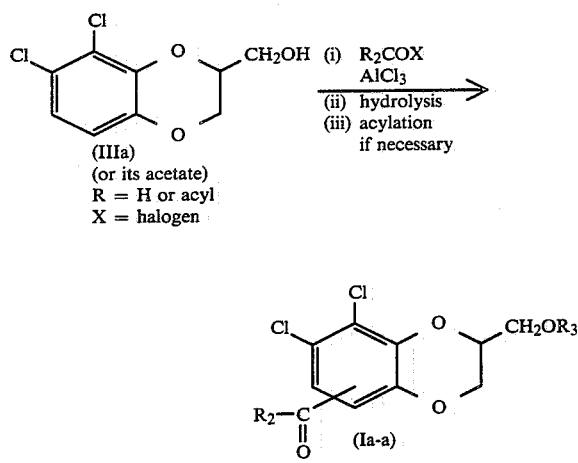

In about 25–30 ml of dry dichloromethane or carbon disulfied are dissolved 8 mmol of a starting material (IIIa) and acylhalide:aluminum chloride (4.0:3.0 equivalent or 5.0:4.0 equivalent), and the solution is stirred at room temperature for 30 minutes and refluxed for 2 hours on an oil bath. After cooled, the reaction mixture is poured into an iced concentrated hydrochloric acid, and extracted three times with dichloromethane. The organic layer is washed with a saturated aqueous solution of sodium chloride, then with 2N sodium hydroxide, and twice with a saturated aqueous solution of sodium chloride, dried over magnesium sulfate and evaporated to give an acyl ester. Subsequently, the acyl ester is refluxed in 2N sodium hydroxide/ethanol for 10 minutes, and the reaction mixture is extracted with dichloromethane to give a mixture of 5-acyl alcohol and 6-acyl alcohol (Ia-a:$R_3$=H). The mixture is, if necessary, separated by acylation into 5-acyl and 6-acyl compounds (Ia-a:$R_3$=acyl).

Process 2 (Method Ab)

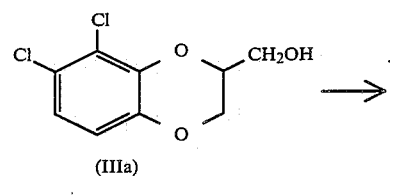

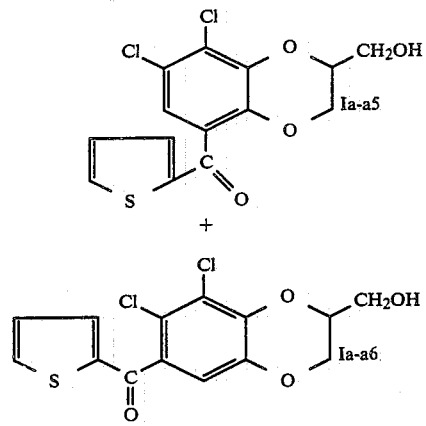

A solution of 3.00 g of the compound (IIIa), 7.5 g (4 equivalent) of 2-thenoyl chloride and 5.2 g (3 equivalent) of aluminium chloride in 30 ml of dry dichloromethane is stirred at room temperature for 30 minutes, then warmed up to 90° C. on an oil bath. The solvent is removed and the mixture is kept at the same temperature for 2.5 hours. After cooled, the reaction mixture is poured into an iced concentrated hydrochloric acid. The separated aqueous layer is extracted three times with dichloromethane, then with a saturated aqueous solution of sodium chloride, with 2N sodium hydroxide and twice with a saturated aqueous solution of sodium chloride, dried over sodium sulfate and then evaporated to give 9.50 g of a residue. A solution of 9.50 g of the residue dissolved in 100 ml of ethanol and 50 ml of 2N sodium hydroxide is refluxed for 30 minutes, the ethanol is evaporated under reduced pressure, and the residue is extracted with dichloromethane three times. The organic layer is washed twice with water, dried over sodium sulfate, and then evaporated to give 4.250 g of a mixture of 2-hydroxymethyl-5-thenoyl-7,8-dichloro-1,4-benzodioxane (Ia-a5) and 2-hydroxymethyl-6-thenoyl-7,8-dichloro-1,4-benzodioxane (Ia-a6). This mixture is separated by using two columns of Lober B (Merck) with dichloromethane:acetone (20:1) as an eluant into 1990 mg of the compound (Ia-a6) as the first half fraction and 2010 mg of the compound (Ia-a5) as the latter half. They are recrystallized from ethanol-hexane to give 1860 mg (yield 42%) of the pure compound (Ia-a6), mp. 113°–114° C. and 1985 mg (yield 45%) of the pure compound (Ia-a5), mp. 122°–125° C., respectively.

Process 2 (General Procedure for Method Ab)

A solution of 8 mmol of the compound (IIIa) and acyl hydride:aluminium chloride (4.0:3.0 equivalent) dissolved in 10–30 ml of anhydrous dichloromethane is stirred at room temperature for 30 minutes then placed on an oil bath and kept at 90° C., at which temperature the solvent is removed. The mixture is kept at 90° C. (bath temperature) for 2.5 hours, and then worked up in the same manner as in the general procedure in Process 2 (Method A) to give the compound (Ia-a).

The compounds prepared according to Method Aa and Method Ab, their reaction conditions and physical constants are shown in Tables 4 and 5.

TABLE 4

Reaction conditions of Method Aa and Method Ab
(A): Method Aa (B): Method Ab

| R2 of alkylating agent | R2COCl:AlCl3 | Reaction conditions | Compd. No. 5-Acyl I a-a, (yield %) | Compd. No. 6-Acyl I a-a, (yield %) |
|---|---|---|---|---|
| m-chlorophenyl | 4.0:3.0 | (B) | 23 (21.0) | 24 (30.6) |
| p-chlorophenyl | 4.0:3.0 | (B) | 25 (46.6) | 26 (42.2) |
| o-fluorophenyl | 4.0:3.0 | (B) | 27 (49.4) | 28 (33.2) |
| o-tolyl | 4.0:3.0 | (B) | 29 (38.0) | 30 (43.8) |
| m-tolyl | 4.0:3.0 | (B) | 31 (40.9) | 3.2 (38.9) |
| p-tolyl | 4.0:3.0 | (B) | 33 (23.1) | 34 (27.8) |
| 2-thienyl | 4.0:3.0 | (B) | 5 (45) | 6 (42) |
| 2-furyl | 4.0:3.0 | (B) | 35 (47) | 36 (48) |
| benzyl | 3.0:3.0 | $CS_2$, r.t., 12 hrs. | 37 (17.4) | 38 (6.3) | r.t.: room temperature

TABLE 5

| compd. I a-a | Position acylated | $R_2$ | $R_3$ | m.p. °C. | Elementary anal. C; Calcd. (%), F; Found (%) | IR(cm$^{-1}$) NMR($\delta$, Hz) |
|---|---|---|---|---|---|---|
| 1 | 5 | Et | H | 126~128 | $C_{12}H_{12}O_4Cl_2$(Mw 291, 134) C H Cl<br>C; 49.51 4.15 24.36<br>F; 49.36 4.17 24.58 | IR$\nu$max(Nujol) 3480,1675,1585<br>NMR($d_6$-acetone) 7.34(1H,s),4.65–4.23(3H,m),<br>3.96~3.85(2H,m),2.98(2H,q,J = 8),2.77(1H,s),1.08 (3H,t,J = 8) |
| 2 | 6 | Et | H | 96~100 | $C_{12}H_{12}O_4Cl_2$(Mw 291, 134) C H Cl<br>C; 49.51 4.15 24.36<br>F; 49.50 4.30 24.43 | IR$\nu$max(Nujol) 3520,1685,1595,1559<br>NMR($d_6$-acetone) 7.07(1H,s),4.70~3,50(6H,m),<br>2.90(2H,q,J = 7.01),1.12(3H,t,J = 7.0) |
| 3 | 5 | Et | Ac | 75~76 | $C_{14}H_{14}O_5Cl_2$(Mw 333, 171) C H Cl<br>C; 50.47 4.24 21.28<br>F; 50.29 4.25 21.56 | IR$\nu$max(Nujol) 1730,1675,1580<br>NMR($d_6$-acetone) 7.34(1H,s), 4.73~4.17(5H,m),<br>2.96(2H,q,J = 8),2.03(3H,s),1.09(3H,t,J = 8) |
| 4 | 6 | Et | Ac | 70~73 | $C_{14}H_{14}O_5Cl_2$(Mw 333, 167) C H Cl<br>C; 50.47 4.23 21.28<br>F; 50.29 4.23 21.21 | IR$\nu$max(Nujol) 1742,1688,1595,1558<br>NMR(CDCl$_3$) 7.00(1H,s),4.67~3.90(5H,m),2.90(2H, q,J = 7),2.10(3H,s),1.17(3H,t,J = 7) |
| 5 | 5 | 2-thienyl | H | 136~137 | $C_{14}H_{10}O_4Cl_2S$(Mw 345, 204) C H Cl S<br>C; 48.71 2.92 20.54 9.29<br>F; 48.79 3.04 20.37 9.11 | IR$\nu$max(Nujol) 3480~3430(br),1630,1582<br>NMR(CDCl$_3$) 7.75(1H,dd,J = 1.5,5.5),7.52(1H,dd,J = 1.5,4.5),7.13(1H,dd,J = 5.5,4.5),7.14(1H,s),<br>4.91~4.06(3H,m),3.92(2H,d,J = 6),2.75(1H,t,J = 7) |
| 6 | 6 | 2-thienyl | H | 113~114 | $C_{14}H_{10}O_4Cl_2S$(Mw 345.2) C H Cl S<br>C; 48.71 2.92 20.54 9.29<br>F; 48.62 3.16 20.54 9.31 | NMR(CDCl$_3$) 7.73(1H,dd,J = 5.1),7.45(1H,dd,J = 5.1),7.17(1H,t,J = 5),6.97(1H,s),3.72~4.28(1H, m),4.30(2H,ABq),3.95(2H,q),2.13(1H,t,J = 7) |
| 7 | 5 | Me | H | 101~102 | $C_{11}H_{10}O_4Cl_2$(Mw 277, 102) C H Cl<br>C; 47.68 3.64 25.59<br>F; 47.53 3.64 25.45 | IR$\nu$max(Nujol) 3500,1683,1580,1550<br>NMR(CDCl$_3$) 7.45(1H,s),4.56~4.18(3H,m),ca.3.96 (2H),2.57(3H,s),2.47(1H,t,J = 7) |
| 8 | 5 | Me | Ac | 69~71 | $C_{13}H_{12}O_6Cl_2$(Mw 319, 144) C H Cl<br>C; 48.93 3.79 22.22<br>F; 48.69 3.82 22.11 | IR$\nu$max(Nujol) 1750,1685,1662,1582<br>NMR(CDCl$_3$) 7.44(1H,s),4.59~4.02(5H,m),2.56(3H, s),2.11(3H,m) |
| 9 | 6 | Me | H | 72~73 | $C_{11}H_{10}O_4Cl_2$(Mw 277, 102) C H Cl<br>C; 47.68 3.64 25.59<br>F; 47.44 3.70 25.55 | IR$\nu$max(Nujol) 3560,1680,1598,1550<br>NMR(CDCl$_3$) 7.10(1H,s),4.45~4.10(3H,m),ca.3.94 (2H),2.60(1H,s),2.39(1H,t,J = 7) |
| 10 | 6 | Me | Ac | 95~96 | $C_{13}H_{12}O_5Cl_2$(Mw 319, 144) C H Cl<br>C; 48.93 3.79 22.22<br>F; 48.82 3.74 22.17 | IR$\nu$max(Nujol) 1740,1680,1590,1560<br>NMR(CDCl$_3$) 7.07(1H,s),4.63~3.95(5H,m),2.58(3H, s),2.10(3H,m) |
| 11 | 5 | propyl | H | 116~118 | $C_{13}H_{14}O_4Cl_2$(Mw 305, 161) C H Cl<br>C; 51.17 4.62 23.23<br>F; 51.11 4.71 23.01 | IR$\nu$max(Nujol) 3470,1655,1575<br>NMR(CDCl$_3$) 7.39(1H,s),4.53~4.16(3H,m),4.01~ 3.88(2H,m),2.90(2H,t,J = 7),2.36(1H,t,J = 6),1.88~ 1.47(2H,m),0.94(3H,t,J = 7) |
| 12 | 6 | propyl | H | 66~68 | $C_{13}H_{14}O_4Cl_2$(Mw 305, 161) C H Cl<br>C; 51.17 4.62 23.24<br>F; 51.03 4.54 23.11 | IR$\nu$max(Nujol) 3440,1690,1595<br>NMR(CDCl$_3$) 6.96(1H,s),4.44~4.08(3H,m),ca.3.93 (2H),2.86(2H,t,J = 7),2.30(1H,t,J = 6),1.75(2H,m), 0.95(3H,t,J = 8) |
| 13 | 5 | isopropyl | H | oil | $C_{13}H_{14}O_4Cl_2$(Mw 305, 161) | IR$\nu$max(CHCl$_2$) 3600,3400(br),1685,1580<br>NMR($d_6$-acetone) 7.23(1H,s),4.63~4.13(3H),ca. 3.90(2H),2.75(1H,s),3.47(1H,m),1.08(6H,d,J = 6) |
| 14 | 5 | n-butyl | H | 80~81 | $C_{14}H_{16}O_4Cl_2$(Mw 319, 188) C H Cl<br>C; 52.68 5.05 22.22<br>F; 52.53 4.85 22.37 | IR$\nu$max(Nujol) 3500,1663,1578<br>NMR(CDCl$_3$) 7.40(1H,s),4.53~4.15(3H),ca.3.95 (2H),2.92(2H,t,J = 7),2.30(1H,t,J = 6),1.79~1.15(2 × 2H),0.90(3H,t,J = 7) |
| 15 | 6 | n-butyl | H | oil | $C_{14}H_{16}O_4Cl_2$(Mw 319, 188) | IR$\nu$max(CHCl$_3$) 3580,3400,1693,1600<br>NMR(CDCl$_3$) 6.97(1H,s),4.46~4.11(3H,m),ca.3.94 (2H),2.90(2H,t,J = 7),2.30(1H,t,J = 6),1.74~1.25(2 × 2H),0.93(3H,t,J = 7) |
| 16 | 5 | cyclopentyl | H | oil | $C_{16}H_{16}O_4Cl_2$(Mw 331, 199) | IR$\nu$max(CHCl$_3$) 3590,3400,1700,1582 |

TABLE 5-continued

| compd. I a-a | Position acylated | R₂ | R₃ | m.p. °C. | Elementary anal. C; Calcd. (%), F; Found (%) | IR(cm⁻¹) NMR(δ, Hz) |
|---|---|---|---|---|---|---|
| 17 | 6 | cyclohexyl | H | oil | | NMR($d_6$-acetone) 7.24(1H,s),4.63~4.14(3H),ca. 3.88(2H),3.70(1H,m),2.89(1H,s),1.86~1.59(8H) IR$\nu$max(CHCl₃) 3570,3370(br),1690,1600 NMR($d_6$-acetone) 6.82(1H,s),4.42~4.06(3H),ca. 3.92(2H),ca.3.0,ca.2.18(2 × 1H),1.95~1.24(1OH) |
| 18 | 5 | benzyl | H | 148~151 | $C_{17}H_{14}O_4Cl_2$(Mw 353, 206) C H Cl C; 57.81 4.00 20.07 F; 57.98 4.08 19.83 | IR$\nu$max(Nujol) 3480,1670,1575 NMR($d_6$-acetone) 7.27(1H,s),7.22(5H,s),4.66~ 4.14(3H),4.26(2H,s),ca.3.87(2H),2.72(1H,s) |
| 19 | 5 | phenyl | H | 158~159 | $C_{16}H_{12}O_4Cl_2$(Mw 339, 178) C H Cl C; 56.66 3.57 20.91 F; 56.55 3.76 20.98 | IR$\nu$max(Nujol) 3430,1643,1590,1572 NMR(CDCl₃) 7.83~7.23(5H),7.07(1H,s),4.44~4.03 (3H),ca.3.89(2H),2.25(1H,t,J = 7) |
| 20 | 6 | phenyl | H | oil | | IR$\nu$max(CHCl₃) 3590,3400,1665,1595 NMR(CDCl₃) 7.86~7.09(5H),6.89(1H,s),4.46~4.13 (3H),4.03~3.90(2H),2.32(1H,t,J = 7) |
| 21 | 5 | o-chloro-phenyl | H | oil | | IR$\nu$max(CHCl₃) 3600,3450~3350,1675 NMR(CDCl₃) ca.7.36(4H),7.29(1H,s),4.37~3.97 (3H),ca.3.85(2H),2.22(1H,t,J = 6) |
| 22 | 6 | o-chloro-phenyl | H | oil | | IR$\nu$max(CHCl₃) 3600,3450~3400(br),1682 NMR(CDCl₃) ca.7.38(4H),7.00(1H,s),4.42~407 (3H),ca.3,92(2H),2.29(1H,br) |
| 23 | 5 | m-chloro-phenyl | H | 96~98 | $C_{16}H_{11}O_4Cl_3$(Mw 373, 628) C H Cl C; 51.44 2.97 28.47 F; 51.13 3.10 28.45 | IR$\nu$max(CHCl₃) 3560,3400~3350(br),1660 NMR(CDCl₃) 7.73~7.22(4H),7.07(1H,s)4.36~4.03 (3H),ca.3.89(2H),2.17(1H,t,J = 6) |
| 24 | 6 | m-chloro-phenyl | H | 144~146 | $C_{16}H_{11}O_4Cl_3$(Mw 373, 628) C H Cl C; 51.44 2.97 28.47 F; 51.54 3.05 28.34 | IR$\nu$max(Nujol) 3530,1655 NMR(CDCl₃) 7.75~7.24(4H),6.87(1H,s),4.45~4.11 (3H),ca.3.94(2H),2.22(1H,t,J = 6) |
| 25 | 5 | p-chloro-phenyl | H | oil | | IR$\nu$max(CHCl₃) 3590,3400~3350(br),1670 NMR($d_6$-acetone) 7.85,7.52(2 × 2H,d,J = 9),7.12 (1H,s),4.50~3.97(3H),ca.3.85(2H),2.74(1H,s) |
| 26 | 6 | p-chloro-phenyl | H | oil | | IR$\nu$max(CHCl₃) 3590,3400~3350(br,1673 NMR($d_3$-acetone) 7.78,7.53(2 × 2H,d,J = 9),6.96 (1H,s),4.56~4.07(3H),ca.3.90(2H),2.75(1H,s) |
| 27 | 5 | o-fluoro-phenyl | H | oil | $C_{16}H_{11}O_4Cl_2F$(Mw 357, 168) | IR$\nu$max(CHCl₃) 3590,3380,1685,1610 NMR(CDCl₃) 7.77~6.94(4H),7.23(1H,s),4.42~4.00 (3H),3.87(2H,t,J = 7),2.33(1H,t,J = 7) |
| 28 | 6 | o-fluoro-phenyl | H | 109~110 | $C_{16}H_{11}O_4Cl_2F$(Mw 357, 168) C H Cl F C; 53.81 3.10 19.85 5.32 F; 53.87 3.18 19.86 5.10 | IR$\nu$max(Nujol) 3420,1665,1610 NMR(CDCl₃) 7.80~7.08(4H,m),6.99(1H,s),4.46~ 4.11(1H,m),ca.4.33(2H),ca.3.95(2H),2.20(1H,t,J = 6) |
| 29 | 5 | o-tolyl | H | oil | | IR$\nu$max(CHCl₃) 3410~3350(br),1660 NMR(CDCl₃) 7.49~7.18(4H),7.11(1H,s),4.43~4.02 (3H),ca.3.89(2H),2.6~2.3(br,1H),2.46(3H,s) |
| 30 | 6 | o-tolyl | H | oil | | IR$\nu$max(CHCl₃) 3570,3400~3350,1662 NMR(CDCl₃) 7.47~7.06(4H),6.91(1H,s),4.42~4.07 (3H),ca.3.91(2H),2.51(3H,s),2.39(1H,t,J = 6) |
| 31 | 5 | m-tolyl | H | oil | | IR$\nu$max(CHCl₃) 3570,3420~3350,1662 NMR(CDCl₃) 7.61~7.23(4H),7.05(1H,s),4.39~3.98 (3H),ca.3.90(2H),2.39(3H,s),ca.2.31(1H) |
| 32 | 6 | m-tolyl | H | oil | | IR$\nu$max(CHCl₃) 3580,3420~3350,1665 NMR(CDCl₃) 7.62~7.23(4H),6.86(1H,s),4.44~4.09 (3H),ca.3.95(2H),2.38(3H,s),ca.2.24(1H) |
| 33 | 5 | p-tolyl | H | oil | | IR$\nu$max(CHCl₃) 3580,3410~3360,1660 NMR(CDCl₃) 7.68,7.22(2 × 2H,d,J = 8),7.03(1H,s), 4.39~3.99(3H),ca.3.89(2H),2.40(3H,s),2.30(1H, t,J = 6) |
| 34 | 6 | p-tolyl | H | oil | | IR$\nu$max(CHCl₃) 3580,3410~3360,1662 NMR(CDCl₃) 7.68,7.22(2 × 2H,d,J = 8),6.85(1H,s), 4.43~4.08(3H),ca.3.93(2H),2.40(3H,s),2.25(1H, t,J = 6) |
| 35 | 5 | 2-furyl | H | 143~145 | $C_{14}H_{10}O_6Cl_2$(Mw 329, 139) C H Cl C; 51.09 3.06 21.54 F; 51.25 3.19 21.78 | IR$\nu$max(Nujol) 3280,1642,1588,1560 NMR(CDCl₃) 7.67(1H,dd,J = 0.5,2.0),7.17(1H,s), 7.13(1H,dd,J = 0.5,4.0),6.56(1H,dd,J = 2.0,4.0), 4.42~4.06(3H),3.93(2H,t,J = 5),2.43(1H,t,j = 6) |
| 36 | 6 | 2-furyl | H | 112~114 | $C_{14}H_{10}O_5Cl_2$(Mw 329, 139) C H Cl C; 51.09 3.06 21.54 F; 51.24 3.13 21.51 | IR$\nu$max(Nujol) 3320~3270,3100,1648,1598 NMR(CDCl₃) 7.64(1H,dd,J = 0.5,2.0),7.07(1H,dd,J = 0.5,4.0),6.95(1H,s),6.50(1H,dd,J = 2.0,4.0), 4.43~4.08(3H),ca.3.93(2H),2.33(1H,t,J = 6) |
| 37 | 5 | benzyl | H | 148~151 | $C_{17}H_{14}O_4Cl_2$(Mw 353, 206) C H Cl C; 57.81 4.00 20.07 F; 57.98 4.08 19.83 | IR$\nu$max(Nujol) 3480,1670,1575 NMR($d_6$-acetone) 7.27(1H,s),7.22(5H,s),4.66~ 4.14(3H,m),4.26(2H,s),4.00~3.75(2H,m),2.72(1H, s) |
| 38 | 6 | benzyl | H | 117~122 | $C_{17}H_{14}O_4Cl_2$ C H Cl C; 57.81 4.00 20.07 | IR$\nu$max(Nujol) 3520,1686,1606,1592 NMR(CDCl₃) 7.23(5H,s),6.90(1H,s),4.47~4.00(3H, m),4.17(2H,s),4.00~3.73(2H,m),2.27~1.86(1H,m) |

TABLE 5-continued

| compd. I a-a | Position acylated | $R_2$ | $R_3$ | m.p. °C. | Elementary anal. C; Calcd. (%), F; Found (%) | IR(cm$^{-1}$) NMR($\delta$, Hz) |
|---|---|---|---|---|---|---|
| | | | | | F; 57.79 3.97 20.09 | |

EXAMPLE 2

Process 1 (Method Ba)

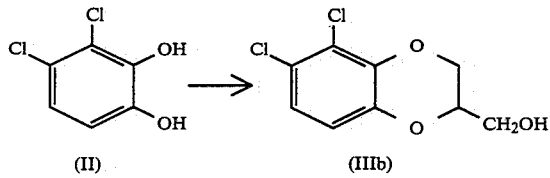

A solution of 5 g of the compound (II), 15.5 g (4 equivalent) of potassium carbonate and 5.75 g (1.5 equivalent) of epibromohydrin in 150 ml of acetone is refluxed for about 10 hours under stirring. After confirmation of disappearance of the starting material spot by thin layer chromatography (TLC, dichloromethane:acetone=20:1), the reaction mixture is filtered in order to remove insoluble material, which is washed well with acetone. The filtrate is evaporated under reduced pressure to give a residue, which is extracted three time with dichloromethane. The organic layer is washed with 2N sodium hydroxide, washed twice with water, dried over sodium sulfate and evaporated to give 6.95 g of a residue, which is chromatographed on 10 g of silica-gel for decolorization and eluted with benzene and with dichloromethane to give 6.30 g of the objective 3-hydroxymethyl-7,8-dichloro-1,4-benzodioxane (IIIb). The physical constants of the compound (IIIb) are shown in Process 1 (Method Bb).

Process 1 (Method Bb)

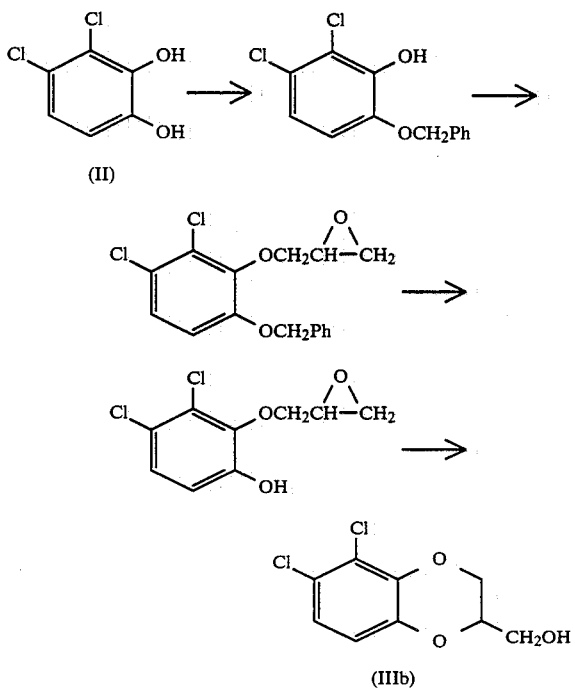

In 250 ml of dimethylformamide is dissolved 8.95 g of the compound (II), and 4.80 g (2 equivalent) of 50% sodium hydride oily suspension and 10.25 g (1.3 equivalent) of benzyl bromide are added thereto. The mixture is stirred for 10 minutes under ice cooling, then poured into 200 ml of water, and sparingly soluble crystals are collected by filtration and recrystallized from hexane to give 2.096 g of 1,2-dibenzyloxy-2-hydroxy-3,4-dichlorobenzene, mp. 74°-75° C.

The filtrate is acidified with hydrochloric acid and extracted twice with 300 ml of ether. The organic layer is washed with water, dried and evaporated to give 10.40 g of a residue, which is chromatographed on a column of 30 g of silica-gel and eluted with dichloromethane to give 8.637 g of 1-benzyloxy-2-hydroxy-3,4-dichlorobenzene as an oil. Yield 64.2%, bp. 155°-160° C.

IR(CHCl$_3$) $\nu$max: 3250, 1600, 1580 cm$^{-1}$.

NMR(CDCl$_3$) $\delta$: about 7.40(5H), 6.92, 6.73(2×1H,d,J=9 Hz), 6.00(1H,s), 5.09(2H,s).

In 180 ml of dry DMF is dissolved 9.73 g of 1-benzoyloxy-2-hydroxy-3,4-dichlorobenzene, and 1.91 g (1.1 equivalent) of 50% sodium hydride oily suspension and 5.45 g (1.1 equivalent) of epibromohydrin are added thereto. The mixture is stirred at 80° C. for 4 hours, then poured into 300 ml of water, and extracted twice with ether. The organic layer is washed with water, dried, and evaporated to give 11.5 g of a residue, which is passed through a column of 40 g of silica-gel to give 10.85 g of a product as a dichloromethane fraction. This is recrystallized from n-hexane to give 9.64 g of 1-benzyloxy-2-(2,3-epoxypropyloxy)-3,4-dichlorobenzene. Yield 82.0%, mp. 59°-61° C.

Anal. Calcd. (%) for C$_{16}$H$_{14}$O$_3$Cl$_2$ (MW. 325.194): C 59.10, H 4.34, Cl 21.80, Found (%): C 59.06, H 4.27, Cl 21.86.

IR(Nujol) $\nu$max: 1580 cm$^{-1}$.

NMR(CDCl$_3$) $\delta$ppm: about 7.36(5H), 7.08, 6.78(2×1H, d, J=9 Hz), 5.05(2H, s), 4.28-3.93(2H), 3.41-3.23(1H), 2.81-2.53(2H).

In 50 ml of ethyl acetate, 1626 mg of 1-benzyloxy-2-(2,3-epoxypropyloxy)-3,4-dichlorobenzene is catalytically hydrogenated with 500 mg of 5% palladium on carbon (50% moisture) under atmospheric pressure (for 2 hours, 153 ml of hydrogen gas absorbed). After removal of the catalyst by filtration, the solvent is evaporated to give 1151 mg of 1-hydroxy-2-(2,3-epoxypropyloxy)-3,4-dichlorobenzene. Yield 98%. The pure product is prepared by recrystallization from cyclohexane. mp. 92°-94° C.

Anal. Calcd. (%) for C$_9$H$_8$O$_3$Cl$_2$ (MW. 235.068): C 45.99, H 3.43, Cl 30.16, Found (%): C 45.36, H 3.54, Cl 29.78.

IR(Nujol) $\nu$max: 3270-3210 (br.), 1590 cm$^{-1}$.

NMR(CDCl$_3$) $\delta$ppm: 7.12, 6.78(2×1H, d, J=9 Hz), 7.9-6.3(1H, br), 4.62-3.98(2H), 3.43-3.30(1H), 3.36-2.96(2H).

To a solution of 1.128 g of 1-hydroxy-2-(2,3-epoxypropyloxy)-3,4-dichlorobenzene dissolved in 10 ml of ethanol is added 4 ml of 2N sodium hydroxide. The mixture is heated at 80° C. for 5 minutes, to which water is then added and extracted with ether. The organic layer is washed with water, then dried and evaporated to give 1.120 g of the objective 3-hydroxymethyl-7,8-dichloro-1,4-benzodioxane (IIb) as an oil. Yield 99%.

IR(CHCl$_3$) $\nu$max: 3590, 3380, 1580 cm$^{-1}$.

NMR(CDCl$_3$) $\delta$ppm: 6.96, 6.75(2×1H, d, J=9 Hz), 4.72–4.01 (2×1H), 3.93–3.80(2H), 2.04(1H, t, J=7 Hz).

Process 2

Compounds of the general formula Ia-b are prepared according to the same manner as in Process 2 (Method Aa and Ab), Example 1. The reaction conditions and the physical constants of the products are shown in Table 6 and Table 7.

TABLE 6

| | Reaction conditions of Method I a-b. (A): Method Aa (B): Method B | | | |
|---|---|---|---|---|
| R$_2$ of alkylating agent | R$_2$COCl:AlCl$_3$ | Reaction conditions | Compd. No. 5-Acyl Ia-b, (yield %) | Compd. No. 6-Acyl Ia-b, (yield %) |
| Et | 6.0:5.0 | (A) | 1 (26.8) | 2 (60.0) |
| n-propyl | 3.0:2.5 | (B) | — | 5 (64.5) |
| 2-thenoyl | 4.0:3.0 | (B) | 6 (16.8) | 7 (44.1) |

TABLE 7

| compd. Ia-b | Position acylated | R$_2$ | R$_3$ | m.p. °C. | Elementary anal. C; Calcd. (%), F; Found (%) | IR(cm$^{-1}$) NMR($\delta$,Hz) |
|---|---|---|---|---|---|---|
| 1 | 5 | Et | Ac | 88~89 | C$_{14}$H$_{14}$O$_6$Cl$_2$(Mw 333, 167) C H Cl<br>C; 50.47 4.24 21.28<br>F; 50.34 4.23 21.42 | IR$\nu$max(Nujol) 1730,1670,1582<br>NMR(CDCl$_3$) 7.40(1H,s),4.52~3.63(5H,m),2.92(2H, q,J = 7),2.08(3H,s),1.15(3H,t,J = 7) |
| 2 | 6 | Et | Ac | oil | | NMR(CDCl$_3$) 7.00(1H,s),4.60~4.07(5H,m),2.90(2H, q,J = 7),2.10(3H,s),1.20(3H,t,J = 7) |
| 3 | 5 | Et | H | 112~114 | C$_{12}$H$_{12}$O$_4$Cl$_2$(Mw 291, 13) C H Cl<br>C; 49.51 4.30 24.53<br>F; 49.25 4.14 24.46 | IR$\nu$max(Nujol) 3510,1668,1576<br>NMR(CDCl$_3$) 7.40(1H,s),4.60~4.17(3H,m),4.05~3.80(2H,m),2.63~2.47(1H,t,J = 7),2.93(2H,q,J = 7), 1.15(3H,t,J = 7) |
| 4 | 6 | Et | H | 84~86 | C$_{12}$H$_{12}$O$_4$Cl$_2$(Mw 291, 13) C H Cl<br>C; 49.51 4.30 24.36<br>F; 49.20 4.21 24.45 | IR$\nu$max(Nujol) 3300,1688,1598,1555<br>NMR(CDCl$_3$) 7.00(1H,s),4.55~4.07(3H,m),3.67~3.57(2H,b),2.87(2H,q,J = 7),2.00(1H,t,J = 7),1.17 (3H,t,J = 7) |
| 5 | 6 | propyl | H | oil | | IR$\nu$max(CHCl$_3$) 3600,3430~3370(br),1690<br>NMR(CDCl$_3$) 6.98(1H,s),4.53~4.09(3H,m),3.94~3.83(2H,m),2.86(2H,t,J = 7),2.20(1H,t,J = 7),1.90~1.50(2H,m),0.95(3H,t,J = 7) |
| 6 | 5 | 2-thienyl | H | oil | | IR$\nu$max(CHCl$_3$) 3450~3400(br),1638<br>NMR(d$_3$-acetone) 7.95(1H,dd,,J = 1.5,5.5),7.64 (1H,dd,J = 1.5,4.5),7.17(1H,dd,J = 5.5,4.5),7.13 (1H,s),4.67~4.16(3H,m),4.68(2H,d,J = 4) |
| 7 | 6 | 2-thieyl | H | 137~139 | C$_{14}$H$_{10}$O$_4$Cl$_2$S(Mw 345.2) C H Cl S<br>C; 48.71 2.92 20.54 9.29<br>F; 48.89 3.02 20.35 9.20 | NMR(CDCl$_3$) 7.73(1H,dd,J = 5.1),7.45(1H,dd,J = 5.1)7.10(1H,t,J = 5),6.95(1H,s),4.13~4.58(3H, br),3.77~4.00(2H,br),2.20(1H,t,J = 7) |

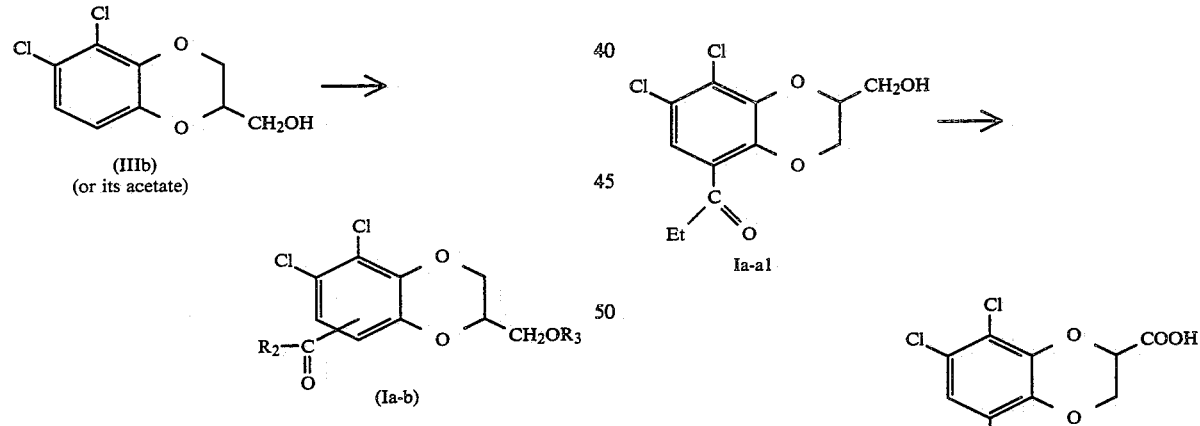

EXAMPLE 3

To a solution of 2.5 g of the compound (Ia-a1) dissolved in 120 ml of acetone is dropwise added 8N chromic acid/sulfuric acid in small portions over a 1.5 hour period. The mixture is allowed to stand overnight at room temperature. The excess amount of the chromic acid is killed by adding methanol, the resulting precipitate is filtered off and washed with acetone, and the filtrate is evaporated under reduced pressure to give crystals. Water is added thereto, and the crystals are collected by filtration. The crystals (2.500 g of crystals; mp. 228°–230° C.) are recrystallized from dichloromethane-ether to give 2.422 g of the objective 5-propionyl-7,8-dichloro-1,4-benzodioxane-2-carboic acid (Ib'-1), mp. 229°–231° C. yield 92%.

General Procedure

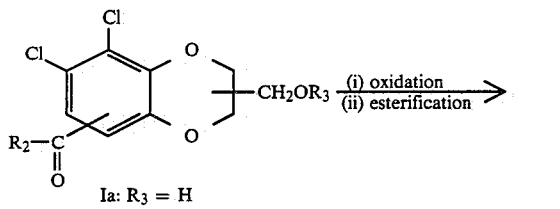

Ia: $R_3 = H$

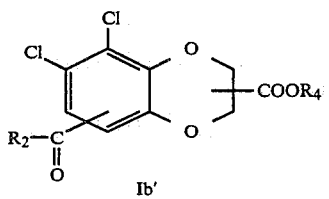

Ib'

To a solution of 2 g of a compound (Ia) ($R_3=H$) dissolved in 100 ml of acetone is dropwise added about 8 ml of 8N chromic acid/sulfuric acid (The reaction solution shows red color immediately after addition; the reagent is added when the red turns green) over a 2 hour period, and the mixture is allowed to stand at room temperature overnight. Excess amount of the chromic acid is killed by addition of methanol, and the precipitate is removed by filtration. The filtrate is evaporated under reduced pressure to give crystals, which are collected by either filtration, or extraction with ethyl acetate or dichloromethane and recrystallized from an appropriate solvent to give a compound (Ib') ($R_4=H$). Further, to a solution of 1.00 g of the compound (Ib') ($R_4=H$) dissolved in 50–70 ml of dry alkanol is added, 0.3–0.5 ml of concentrated sulfuric acid, and the mixture is refluxed for about 3–5 hours and evaporated under reduced pressure. The residue is extracted three time with dichloromethane and the organic layer is, washed twice with a saturated aqueous solution of sodium chloride, dried over sodium sulfate and then evaporated to give a residue, which is recrystallized from an appropriate solvent to give a compound (Ib') ($R_4=$alkyl). Compounds (Ib') prepared in the same procedure as above and their physical constants are shown in Table 8.

TABLE 8

| Compd. I a-b' | Position of —COR$_2$ | Position of —COOR$_4$ | R$_2$ | R$_4$ | mp. °C. | Elementary Anal. C; Calcd. (%), F; Found (%) | IR(cm$^{-1}$) NMR(δ, Hz) |
|---|---|---|---|---|---|---|---|
| 1 | 5 | 2 | Et | H | 231~233 | C$_{12}$H$_{10}$O$_5$Cl$_2$(Mw 305, 117)<br>C  H  Cl<br>C; 47.24  3.30  23.24<br>F; 47.28  3.48  23.11 | IRνmax(Nujol) 3170~3150, 1763, 1670, 1580<br>NMR(d$_6$-acetone) 7.34(1H,s), 7.0~5.5(1H,b), 5.28 (1H, t, J = 3), 4.76, 4.48( 1H, dd, J = 13.3), 2.92(2H, q, J = 8), 1.07(3H, t, J = 8) |
| 2 | 5 | 2 | Me | H | 206~208 | C$_{11}$H$_6$O$_5$Cl$_2$(Mw 291,09)<br>C  H  Cl<br>C; 45.39  2.77  24.36<br>F; 45.14  2.98  24.56 | IRνmax(Nujol) 3400~2200(b), 1740, 1683, 1583<br>NMR(d$_6$-acetone) 7.38(1H,s), 7.1~6.4(1H,b), 5.33 (1H, t, J = 3), 4.81, 4.55( 1H, dd, J = 13.3), 2.53(3H,s) |
| 3 | 5 | 2 | n-propyl | H | 177~178 | C$_{13}$H$_{12}$O$_5$Cl$_2$(Mw 319, 144)<br>C  H  Cl<br>C; 48.93  3.79  22.22<br>F; 49.13  3.89  22.17 | IRνmax(Nujol) 3300~2500(b), 1770, 1655<br>NMR(d$_6$-acetone) 8.6~7.5(1H,b), 7.36(1H,s), 5.52 (1H, t, J = 3), 4.80, 4.53( 1H, dd, J = 3.13), 2.92(2H, t, J = 7), 1.64(2H,m), 0.91(3H, t, J = 7) |
| 4 | 5 | 2 | isopropyl | H | 150~152 | C$_{13}$H$_{12}$O$_6$Cl$_2$(Mw 319, 144)<br>C  H  Cl<br>C; 48.93  3.79  22.22<br>F; 49.08  3.73  22.45 | IRνmax(Nujol) 3500~2300(b), 1760, 1645<br>NMR(d$_6$-acetone) 8.5~6.8(1H,b), 7.26(1H,s), 5.33 (1H, t, J = 3), 4.78, 4.51( 1H, dd, J = 3.13), 3.42(1H, m), 1.07(6H, dd, J = 10.7) |
| 5 | 5 | 2 | n-butyl | H | 151~152 | C$_{14}$H$_{14}$O$_5$Cl$_2$(Mw 333, 171)<br>C  H  Cl<br>C; 50.47  4.24  21.28<br>F; 50.23  4.21  21.28 | IRνmax(Nujol) 3500~2300(b), 1738, 1675<br>NMR(d$_6$-acetone) 8.0~6.8(1H,b), 7.34(1H,s), 5.31 (1H, t, J = 3), 4.78, 4.52( 1H, dd, J = 3.13), 1.77~1.06 (2 × 2H), 0.88(3H, t, J = 7) |
| 6 | 5 | 2 | cyclopentyl | H | 149~150 | C$_{15}$H$_{14}$O$_5$Cl$_2$(Mw 345, 182)<br>C  H  Cl<br>C; 52.19  4.09  20.54<br>F; 52.13  4.01  20.56 | IRνmax(Nujol) 3550~2200(b), 1722, 1672<br>NMR(d$_6$-acetone) 7.26(1H,s), 6.0~4.9(1H,b), 5.29 (1H, t, J = 3), 4.76, 4.48( 1H, dd, J = 3.13), 3.65(1H, m), 1.85~1.57(8H) |
| 7 | 5 | 2 | benzyl | H | 171~173 | C$_{17}$H$_{12}$O$_5$Cl$_2$(Mw 367, 189)<br>C  H  Cl<br>C; 55.61  3.29  19.31<br>F; 55.93  3.35  19.25 | IRνmax(Nujol) 3300~2400(br), 1730, 1683<br>NMR(d$_6$-acetone) 7.7~6.8(1H,br), 7.30(1H,s), 7.22(5H,s), 5.30(1H, t, J = 3), 4.71, 4.48(2 × 1H, dd, J = 3.13), 4.25(2H,s) |
| 8 | 5 | 2 | phenyl | H | 218~219 | C$_{16}$H$_{10}$O$_5$Cl$_2$(Mw 353, 161)<br>C  H  Cl<br>C; 54.42  2.85  20.08<br>F; 54.35  3.13  19.99 | IRνmax(Nujol) 3500~2200(b), 1760, 1630<br>NMR(d$_6$-acetone) 8.7~7.7(1H,b), 7.83~7.35(5H), 7.13(1H,s), 5.27(1H, t, J = 3) 4.48, 4.21( 1H, dd, J = 3.13) |
| 9 | 5 | 2 | O—chlorophenyl | H | 214~215 | C$_{16}$H$_9$O$_5$Cl$_3$(Mw 387, 606)<br>C  H  Cl<br>C; 49.58  2.34  27.44<br>F; 49.76  2.53  27.67 | IRνmax(Nujol) 3600~2300(br), 1758, 1622<br>NMR(d$_6$-acetone) 10.3~9.0(1H,b,), ca. 7.46(4H), 7.33(1H,s), 5.22(1H, t, J = 3), 4.41, 4.22(2 × 1H, dd, J = 3.12) |
| 10 | 5 | 2 | m-chlorophenyl | H | 176~177 | C$_{16}$H$_9$O$_5$Cl$_3$(Mw 387, 606)<br>C  H  Cl<br>C; 49.58  2.34  27.44<br>F; 49.68  2.62  27.11 | IRνmax(Nujol) 3600~2000(br), 1760, 1640<br>NMR(d$_6$-acetone) 7.77~7.30(4H), 8.5~7.1(1H,br), 7 .17(1H,s), 5.27(1H, t, J = 3), 4.51, 4.32(2 × 1H, dd, J = 3.12) |
| 11 | 5 | 2 | p-chlorophenyl | H | 241~242 | C$_{16}$H$_9$O$_5$Cl$_3$(Mw 387, 606)<br>C  H  Cl<br>C; 49.58  2.34  27.44<br>F; 49.67  2.60  27.25 | IRνmax(Nujol) 3600~2400(br), 1768, 1642<br>NMR(d$_6$-acetone) 8.1~6.7(1H,br), 7.81, 7.52(2 × 2H, d, J = 9), 7.17(1H,s), 5.29(1H, t, J = 3), 4.53, 4.33 (2 × 1H, dd, J = 3.12) |
| 12 | 5 | 2 | o-fluorophenyl | H | 225~227 | C$_{16}$H$_9$O$_5$Cl$_2$F(Mw 371, 151)<br>C  H  Cl  F<br>C; 51.78  2.44  19.10  5.12<br>F; 51.85  2.56  19.01  5.09 | IRνmax(Nujol) 3160~3060(br), 1760, 1620<br>NMR(d$_6$-acetone) 7.74~7.04(4H), 7.27(1H,s), ca. 6.26(1H, t, J = 3), 4.45, 4.25( 1H, dd, J = 3.13) |
| 13 | 5 | 2 | o-tolyl | H | 212~213 | C$_{17}$H$_{12}$O$_5$Cl$_2$(Mw 367, 189)<br>C | IRνmax(Nujol) 3600~2200(br), 1758, 1620<br>NMR(d$_6$-acetone) 9.3~7.8(1H,br), 7.53~7.26(4H), 7 |

TABLE 8-continued

| Compd. 1 a-b' | Position of —COR$_2$ | Position of —COOR$_4$ | R$_2$ | R$_4$ | mp. °C. | Elementary Anal. C; Calcd. (%), F; Found (%) | | | IR(cm$^{-1}$), NMR(δ, Hz) |
|---|---|---|---|---|---|---|---|---|---|
| 14 | 5 | 2 | m-tolyl | H | 194~195 | C; F; | 55.61 56.32 | 3.29 3.42 | 19.31 18.79 | .19(1H,s), 5.25(1H, t, J = 3), 4.46, 4.27(2 × 1H, dd, J = 3.12), 2.46(3H,s) IRνmax(Nujol) 3500~2100(br), 1765, 1637 NMR(d$_6$-acetone) 10.1~8.7(1H,br), 7.61~7.31 (4H), 7.11(1H,s), 5.26(1H, t, J = 3), 4.49, 4.30(2 × 1H, dd, J = 3.12), 2.35(3H,s) |
| 15 | 5 | 2 | p-tolyl | H | 212~214 | C$_{17}$H$_{12}$O$_5$Cl$_2$(Mw 367, 189) C H Cl C; F; | 55.61 55.44 | 3.29 3.40 | 19.31 19.22 | IRνmax(Nujol) 3400~2100(br), 1755, 1623 NMR(d$_6$-acetone) 9.4~7.4(1H,br), 7.67, 7.27(2 × 2H, d, J = 8), 7.09(1H,s), 5.26(1H, t, J = 3), 4.48, 4.30 (2 × 1H, dd, J = 3.12), 2.38(3H,s) |
| 16 | 5 | 2 | 2-thienyl | H | 215~217 | C$_{17}$H$_{12}$O$_5$Cl$_2$(Mw 367, 189) C H Cl C; F; | 55.61 55.68 | 3.29 3.34 | 19.31 19.19 | IRνmax(Nujol) 3400~2000(b), 1765, 1620 NMR(d$_6$-acetone) 8.8~7.8(1H,b), 7.94(1H, dd, J = 1.5,5.5),7.53(1H, dd,J = 1.5,4.5), 7.15(1H,d, d. J = 4.5, 5.5), 7.15(1H,s), 5.28(1H, t, J = 3), 4.58, 4.37 ( 1H, dd, J = 3.13) |
| | | | | | | C$_{14}$H$_6$O$_5$Cl$_2$S(Mw 359, 187) C H Cl S C; F; | 46.82 47.10 | 2.24 2.65 | 19.74 19.41 | 8.93 8.52 |
| 17 | 5 | 2 | 2-furyl | H | 160~162 | C$_{14}$H$_6$O$_5$Cl$_2$(Mw 343, 122) C H Cl ; ; | 49.01 49.41 | 2.35 2.70 | 20.66 20.43 | IRνmax(Nujol) 3140, 1760, 1638, 1585 NMR(d$_6$-acetone) 8.5~7.5(1H,b), 7.87(1H, dd, J = 0.5, 2.0), 7.19(1H,s), 7.18(1H, dd, J = 0.5, 2.0), 6.66 (1H, dd, J = 2.0, 4.0), 5.31(1H, t, J = 3), 4.61, 4.39 (2 × 1H, dd, J = 3) |
| 18 | 5 | 3 | Et | H | 173~175 | C$_{12}$H$_{10}$O$_5$Cl$_2$(Mw 305, 113) C H Cl C; F; | 47.24 47.17 | 3.30 3.46 | 23.24 23.18 | IRνmax(Nujol) 3080, 1740, 1715, 1682, 1580 NMR(d$_6$-acetone) 8.33~7.50(1H,b), 7.40(1H,s), 5.37(1H, t, J = 3), 4.43~4.95(2H,m), 3.08(2H, q, J = 7), 1.10(3H, t, J = 7) |
| 19 | 5 | 3 | 2-thienyl | H | non-crystal | C$_{14}$H$_6$O$_5$Cl$_2$S(Mw 359, 187) Mass M$^+$ 358 | | | | IRνmax(Nujol) 3600~2200(br), 1730, 1630 NMR(d$_6$-acetone) 9.0~8.0(1H,br), 7.94(1H, dd, J = 1.5, 5.5), 7.78(1H, dd, J = 1.5, 4.5), 7.17(1H,s), 7.16 (1H, dd, J = 4.5, 5.5), 5.12(1H, t, J = 3), 4.78, 4.47(2 × 1H, dd, J = 3) |
| 20 | 6 | 2 | H | H | 262~263 | C$_{10}$H$_6$O$_5$Cl$_2$(Mw 277, 059) C H Cl C; F; | 43.35 43.07 | 2.18 2.36 | 25.59 25.53 | IRνmax(Nujol) 1755, 1658, 1593, 1558 NMR(d$_6$-acetone) 10.33(1H,s), 7.35(1H,s), 5.40 (1H, t, J = 3), 4.75~4.33(2H,m) |
| 21 | 6 | 2 | Me | H | 199~200 | C$_{11}$H$_6$O$_5$Cl$_2$(Mw 291, 090) C H Cl C; F; | 45.39 45.11 | 2.77 2.92 | 24.36 24.09 | IRνmax(Nujol) 3400~2100(br), 1763, 1680, 1665 NMR(d$_6$-acetone) 7.16(1H,s), 7.1~6.5(1H,br), 5.31(1H, t, J = 3), 4.68, 4.41(2 × 1H, dd, J = 13.3), 2.56 (3H,s) |
| 22 | 6 | 2 | Et | H | 177~179 | C$_{12}$H$_{10}$O$_5$Cl$_2$(Mw 305, 113) C H Cl C; F; | 47.24 47.02 | 3.30 3.07 | 23.24 23.45 | IRνmax(Nujol) 1754, 1710, 1600 NMR(d$_6$-acetone) 7.09(1H,br), 4.78~4.33(2H,m), 2.92(2H, q, J = 7), 1.11(3H, t, J = 7) |
| 23 | 6 | 2 | n-propyl | H | 132~133 | C$_{13}$H$_{12}$O$_5$Cl$_2$(Mw 319, 144) C H Cl C; F; | 48.93 48.63 | 3.79 3.59 | 22.22 22.12 | IRνmax(Nujol) 3600~2000(br), 1740, 1700 NMR(CDCl$_3$) 9.52(1H,s), 6.97(1H,s), 5.07(1H, t, J = 3), 4.58, 4.32(2 × 1H, dd, J = 3.13), 2.87(2H, t, J = 7), 1.70(2H,m), 0.96(3H, t, J = 7) |
| 24 | 6 | 2 | n-butyl | H | oil | C$_{14}$H$_{14}$O$_5$Cl$_2$(Mw 333, 171) | | | | IRνmax(CHCl$_3$) 3600~2400(br), 1738, 1690 NMR(CDCl$_3$) 8.20(1H,br), 6.94(1H,s), ca. 5.04(1H), 4.63~4.21(2H), 2.87(2H, t, J = 7), 1.82~1.11(2 × 2H), 0.91(3H, t, J = 7) |
| 25 | 6 | 2 | phenyl | H | 201~204 | C$_{16}$H$_{10}$Cl$_2$O$_5$(Mw 353, 157) | | | | IRνmax(Nujol) 3160, 1760, 1650 |

TABLE 8-continued

| Compd. I a-b' | Position of —COR2 | Position of —COOR4 | R2 | R4 | mp. °C. | Elementary Anal. C; Calcd. (%) F; Found (%) | | | | IR(cm⁻¹), NMR(δ, Hz) |
|---|---|---|---|---|---|---|---|---|---|---|
| | | | | | | | C | H | Cl | |
| 26 | 6 | 2 | o-chlorophenyl | H | 149~150 | C; F; | 54.42 54.13 | 2.85 2.93 | 20.08 20.36 | NMR(d₆-acetone) 7.87~7.33(5H,m), 6.95(1H,s), 5.32(1H, t, J = 3), 4.83~4.30(2H,m) |
| 27 | 6 | 2 | m-chlorophenyl | H | 198~200 | | C₁₆H₉O₅Cl₃(Mw 387, 606) Mass M⁺ 386 | | | IRνmax(Nujol) 3600~2200(br), 1723, 1675 NMR(d₆-acetone) 11.0~9.3(1H,br), ca. 7.51(4H), 7.01(1H,s), 5.33(1H, t, J = 3), 4.68, 4.42(2 × 1H, dd, J = 3.12) |
| | | | | | | | C | H | Cl | |
| | | | | | | C; F; | 49.58 49.47 | 2.34 2.48 | 27.44 27.25 | IRνmax(Nujol) 3600~2000(br), 1758, 1667 NMR(d₆-acetone) 8.8~7.7(1H,br), 7.76~7.43(4H), 7.01 (1H,s), 5.33(1H, t, J = 3), 4.69, 4.45(2 × 1H, dd, J = 3.12) |
| 28 | 6 | 2 | p-chlorophenyl | H | 152~154 | | C₁₆H₉O₅Cl₃(Mw 387, 606) | | | IRνmax(Nujol) 3650~2200(br), 1765, 1660 NMR(d₆-acetone) 7.77, 7.53(2 × 2H, d, J = 9), 7.4~6.3 (1H,br), 6.96(1H,s), 5.30(1H, t, J = 3), 4.67, 4.42(2 × 1 H, dd, J = 3.12) |
| | | | | | | | C | H | Cl | |
| | | | | | | C; F; | 49.58 49.26 | 2.34 2.67 | 27.44 27.21 | |
| 29 | 6 | 2 | o-fluorophenyl | H | 197~199 | | C₁₆H₉O₅Cl₂F(Mw 371, 151) | | | IRνmax(Nujol) 3600~2100(br), 1720, 1680 NMR(d₆-acetone) 8.5~7.0(1H,br), 7.80~7.12(4H, m), 7.03(1H,s), 5.33(1H, t, J = 3), 4.70, 4.45(2 × 1H, dd, J = 3.13) |
| | | | | | | | C | H | Cl | F |
| | | | | | | C; F; | 51.78 51.52 | 2.44 2.64 | 19.10 19.30 | 5.12 5.16 |
| 30 | 6 | 2 | 2-thienyl | H | 192~194 | | C₁₄H₅O₆Cl₂S(Mw 359, 184) | | | IRνmax(Nujol) 3475, 3400, 1720, 1710, 1620 NMR(d₆-acetone) 8.00(1H, dd, J = 5.1), 7.50(1H, dd, J = 5.1), 7.17(1H, t, J = 5), 7.03(1H, s), 5.30(1H, t, J = 4), 4.30~4.83(2H, m) |
| | | | | | | | C | H | S | Cl |
| | | | | | | C; F; | 46.81 46.88 | 2.25 2.36 | 8.93 8.9 | 19.74 19.58 |
| 31 | 6 | 2 | 2-furyl | H | 142~145 | | C₁₄H₆O₅Cl₂.H₂O(Mw 361, 138) | | | IRνmax(Nujol) 3480, 3410, 1720, 1650 NMR(d₆-acetone) 7.88(1H, dd. J = 0.5, 2.0), 7.16 (1H, dd, J = 0.5, 4.0), 7.04(1H,s), 6.67(1H, dd, J = 2.0, 4.0), ca. 5.80(1H), 5.30(1H, t, J = 3), 4.68, 4.42(2 × 1H, dd, J = 3.13) |
| | | | | | | | C | H | Cl | |
| | | | | | | C; F; | 46.56 47.30 | 2.79 2.84 | 19.63 19.62 | |
| 32 | 6 | 2 | cyclohexyl | H | oil | | C₁₆H₁₈O₅Cl₂(Mw 359, 209) Mass M⁺ 358 | | | IRνmax(CHCl₃) 3600~2300(br), 1735, 1690 NMR(CDCl₃) 7.73(1H,br,s), 6.82(1H,s), 5.03(1H, t, J = 3), 4.56, 4.29(2 × 1H, dd, J = 3.12), ca. 2.98(1H), 1.95~1.24(OH) |
| 33 | 6 | 2 | o-tolyl | H | 187~188 | | C₁₇H₁₂O₅Cl₂(Mw 367, 189) | | | IRνmax(Nujol) 3500~2300(br), 1758, 1645 NMR(d₆-acetone) 10.0~8.5(1H,br), 7.57~7.16 (4H), 6.96(1H,s), 5.33(1H, t, J = 3), 4.69, 4.44(2 × 1H, dd, J = 3.12), 2.49(3H,s) |
| | | | | | | | C | H | Cl | |
| | | | | | | C; F; | 55.61 55.59 | 3.29 3.33 | 19.31 19.47 | |
| 34 | 6 | 2 | m-tolyl | H | 205~206 | | C₁₇H₁₂O₅Cl₂(Mw 367, 189) | | | IRνmax(Nujol) 3210~3180, 1760, 1652 NMR(d₆-acetone) 10.4~8.9(1H,br), 7.63~7.23 (4H), 6.93(1H,s), 5.31(1H, t, J = 3), 4.68, 4.44(2 × 1H, dd, J = 3.12), 2.37(3H,s) |
| | | | | | | | C | H | Cl | |
| | | | | | | C; F; | 55.61 55.71 | 3.29 3.34 | 19.31 19.06 | |
| 35 | 6 | 2 | p-tolyl | H | 188~189 | | C₁₇H₁₂O₅Cl₂(Mw 367, 189) | | | IRνmax(Nujol) 3400~2100(br), 1750, 1640 NMR(d₆-acetone) 9.5~8.3(1H,br), 7.64, 7.30(2 × 2H, d, J = 8), 6.89(1H,s), 5.28(1H, t, J = 3), 4.66, 4.42 (2 × 1H, dd, J = 3.12), 2.37(3H,s) |
| | | | | | | | C | H | Cl | |
| | | | | | | C; F; | 55.61 55.53 | 3.29 3.33 | 19.31 19.35 | |
| 36 | 6 | 3 | n-propyl | H | 124~125 | | C₁₃H₁₂O₅Cl₂(Mw 319, 144) | | | IRνmax(CDCl₃) 9.65(1H,s), 7.07(1H,s), 4.94(1H, t, J = 3), 4.67, 4.46(2 × 1H, dd, J = 3.13), 2.87(2H, t, J = 7), 1.91~1.50(2H,m), 0.95(3H, t, J = 7) |
| | | | | | | | C | H | Cl | |
| | | | | | | C; F; | 48.93 48.84 | 3.79 3.54 | 22.22 22.20 | |
| 37 | 6 | 3 | o-etoxyphenyl | H | 206~208 | | C₁₃H₁₄O₅Cl₂(Mw 397, 215) | | | IRνmax(Nujol) 3600~2200(br), 1710, 1643 NMR(d₆-acetone) 7.78~6.93(4H,m), 6.95(1H,s), 7.4~6.0(1H,br), 5.17(1H, t, J = 3), 4.76, 4.50(2 × 1H, |
| | | | | | | | C | H | Cl | |
| | | | | | | C; | 54.43 | 3.55 | 17.85 | |

TABLE 8-continued

| Compd. Ia-b' | Position of —COR$_2$ | Position of —COOR$_4$ | R$_2$ | R$_4$ | mp. °C. | Elementary Anal. C; Calcd. (%), F; Found (%) | | | IR(cm$^{-1}$) NMR(δ, Hz) |
|---|---|---|---|---|---|---|---|---|---|
| 38 | 6 | 3 | o-fluorophenyl | H | 162~163 | C$_{16}$H$_9$O$_5$Cl$_2$F(Mw 371, 151) C 54.27 H 3.54 F 17.74; F: C 51.78 H 2.44 F 19.10 5.12; 51.55 2.65 19.65 4.95 | | | dd, J = 3.13), 3.90(2H, q, J = 7), 0.93(3H, t, J = 7) IRνmax(Nujol) 3600~2200(br), 1758, 1630 NMR(d$_6$-acetone) 9.4~7.3(1H,br), 7.83~7.23(4H, m), 7.15(1H,s), 5.12(1H, t, J = 3), 4.79, 4.58(2 × 1H, dd, J = 3.13) |
| 39 | 6 | 3 | phenyl | H | 207~209 | C$_{16}$H$_{10}$Cl$_2$O$_5$(Mw 353, 157) C 54.42 H 2.85 Cl 20.08; 54.19 3.03 20.23 | | | IRνmax(Nujol) 1720, 1670, 1590 NMR(d$_6$-acetone) 8.22~7.48(5H,m), 7.07(1H,s), 5.22(1H, t, J = 3), 4.95~4.45(2H,m) |
| 40 | 6 | 3 | 2-thienyl | H | 220~222 | C$_{14}$H$_6$O$_5$Cl$_2$S(Mw 359, 184) C 46.81 H 2.25 Cl 19.74 S 8.93; 46.74 2.56 19.80 8.85 | | | IRνmax(Nujol) 1730, 1620, 1600 NMR(d$_6$-acetone) 8.03(1H, dd, J = 5.1), 7.53(1H, dd, J = 5.1), 7.23(1H, t, J = 5), 7.17(1H,s), 5.23(1H, t, J = 4), 4.68(2H, t, J = 4) |
| 41 | 5 | 2 | Et | Et | 108~109 | C$_{14}$H$_{10}$O$_5$Cl$_2$(Mw 333, 171) C 50.47 H 4.24 Cl 21.28; 50.35 4.33 21.54 | | | IRνmax(Nujol) 1735, 1670, 1580 NMR(d$_6$-acetone) 7.34(1H,s), 5.29(1H, t, J = 3), 4.75, 4.48(2 × 1H, dd, J = 3.13), 4.21, 2.91(2 × 2H, q, J = 8), 1.23, 1.07(2 × 3H, t, J = 8) |
| 42 | 5 | 2 | phenyl | Et | 171~172 | C$_{18}$H$_{14}$O$_5$Cl$_2$(Mw 381, 216) C 56.71 H 3.70 Cl 18.60; 56.34 3.81 18.62 | | | IRνmax(Nujol) 1742, 1658 NMR(d$_6$-acetone) 7.85~7.42(5H), 7.16(1H,s), 5.29 (1H, t, J = 3), 4.49, 4.31(2 × 1H, dd, J = 3.12), 4.22(2H, q, J = 7), 1.20(3H, t, J = 7) |
| 43 | 5 | 2 | 2-thienyl | Et | 124~125 | C$_{16}$H$_{12}$O$_5$Cl$_2$S(Mw 387, 237) C 49.63 H 3.12 Cl 18.31 S 8.28; 49.30 3.28 18.33 | | | IRνmax(CDCl$_3$) 7.72(1H, dd, J = 6.2), 7.47(1H, dd, J = 6.2), 7.10(1H, t, J = 6), 7.17(1H,s), 5.00(1H, t, J = 4), 4.62~4.17(2H,m), 4.27(2H, q, J = 8), 1.27(3H, t, J = 8) |
| 44 | 5 | 3 | Et | Et | 73~74 | C$_{14}$H$_{14}$O$_5$Cl$_2$(Mw 333, 167) C 50.47 H 4.24 Cl 21.28; 50.29 4.26 21.31 | | | IRνmax(Nujol) 3080, 1740, 1678, 1582 NMR(d$_6$-acetone) 7.33(1H,s), 5.30(1H, t, J = 4), 4.72~4.40(2H,m), 4.23(2H, q, J = 8), 3.05(2H, q, J = 8), 1.23(3H, t, J = 8), 1.15(3H, t, J = 8) |
| 45 | 6 | 3 | o-fluorophenyl | Et | 139~140 | C$_{18}$H$_{13}$O$_5$Cl$_2$F(Mw 399, 206) C 54.16 H 3.28 Cl 17.76 F 4.76; 53.93 3.36 17.76 4.78 | | | IRνmax(CDCl$_3$) 7.82~6.98(4H,m), 7.10(1H,s), 4.86(1H, t, J = 3), ca. 4.53(2H), 4.27(2H, q, J = 7), 1.27(3H, t, J = 7) |
| 46 | 6 | 3 | phenyl | Et | 112~113 | C$_{18}$H$_{14}$Cl$_2$O$_5$(Mw 381, 211) C 56.71 H 3.10 Cl 18.60; 56.66 3.60 18.57 | | | IRνmax(Nujol) 1743, 1667, 1600, 1557 NMR(d$_6$-acetone) 7.05(1H,s), 7.88~7.47(5H,m), 5.20(1H, t, J = 4.0), 4.90~4.43(2H,m), 4.23(2H, q, J = 7.0), 1.23(3H, t, J = 7.0) |
| 47 | 6 | 3 | 2-thienyl | Et | 137~138 | C$_{16}$H$_{12}$O$_5$Cl$_2$S(Mw 387, 237) C 49.63 H 3.12 Cl 18.31 S 8.28; 49.65 3.10 18.19 | | | IRνmax(Nujol) 1750, 1658, 1588 NMR(d$_6$-acetone) 7.23(1H,s), 8.10(1H, dd, J = 5.0, 1.0), 7.58(1H, dd), 7.30(1H, t, J = 5.0), 5.27(1H, t, J = 4.0), 4.70(2H, t, J = 4.0), 4.30(2H, q, J = 7.0), 1.27 (3H, t, J = 7.0) |
| 48 | 6 | 2 | phenyl | Et | 71~73 | C$_{18}$H$_{14}$O$_5$Cl$_2$(Mw 381, 211) C 56.71 H 3.70 Cl 18.60; 56.56 3.83 18.57 | | | NMR(CDCl$_3$) 5.80(1H,s), 7.90, 7.17(5H,m), 5.00(1H, t, J = 5.0) ca. 4.43(2H,m), 4.27(2H, q, J = 7.0), 1.30 (3H, t, J = 7.0) |
| 49 | 6 | 2 | 2-thienyl | Et | 134~135 | C$_{18}$H$_{12}$O$_5$Cl$_2$S(Mw 387, 237) C 49.63 H 3.12 Cl 8.28 S 18.31; 49.46 3.25 8.24 18.15 | | | NMR(d$_6$-acetone) 7.01(1H,s), 8.03(1H, dd, J = 5.0, 1.0), 7.52(1H, t, J = 5.0, 1.0), 7.22(1H, t, J = 5.0) 5.33(1H, t, J = 4.0), 4.33~4.87(2H,m), 4.27(2H, q, J = 7.0), 1.27(3H, t, J = 7.0) |

EXAMPLE 4

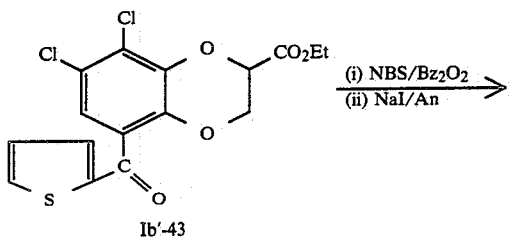

Ib'-43

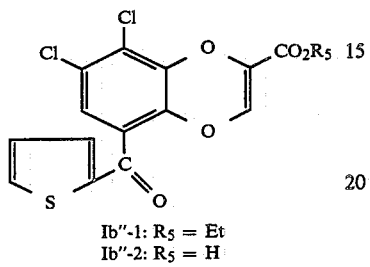

Ib''-1: $R_5$ = Et
Ib''-2: $R_5$ = H

A solution of 1.500 g of the compound (Ib'-43), 2.500 g of N-bromosuccinimide (about 3.5 equivalent) and 230 mg of benzoyl peroxide dissolved in 80 ml of dry carbon tetrachloride is refluxed for about 20 hours. After removal of the precipitate by filtration, the filtrate is evaporated under reduced pressure to give a residue, 3.0 g Of sodium iodide and 100 ml of acetone are added to the residue, and the mixture is refluxed for 1.5 hours. The reaction mixture is filtered in order to remove the precipitate and then the filtrate is evaporated under reduced pressure, and extracted three times with dichloromethane. The organic layer is washed twice with an aqueous solution of sodium thiosulfate, then with water, dried over sodium sulfate and evaporated to give 1.80 g of a residue, which is recrystallized from ethanol to give 1.100 g of the objective 2-epoxycarbonyl-5-thenoyl-7,8-dichloro-1,4-benzodioxine (Ib''-1). Yield 73%, mp. 165°–166° C.

Anal. Calcd. (%) for $C_{16}H_{10}O_5Cl_2S$ (MW. 385.221): C 49.89, H 2.62, Cl 18.41, S 8.32 Found (%): C 49.91, H 2.75, Cl 18.70, S 8.32.

IR(Nujol) $\nu$max: 3150, 3100, 1735, 1690, 1675, 1630, 1599, 1575 cm$^{-1}$.

NMR(CDCl$_3$) $\delta$ppm: 7.77(1H, d, d, J=6.2), 7.53(1H, d, d, J=6.2), 7.12(1H, t, J=6.2), 7.12(1H, s,), 6.90(1H, s), 4.27(2H, q, J=8), 1.47(3H, t, J=8).

To a solution of 742 mg of the compound (Ib''-1) dissolved in 10 ml of dioxane, is added 3 ml of 1N sodium hydroxide. The mixture is heated at 70°–80° C. for 5–10 minutes and then allowed to stand for 1 hour. After neutralized with hydrochloric acid, the reaction mixture is extracted twice with ethyl acetate. The organic layer is washed twice with a saturated aqueous solution of sodium chloride, dried over sodium sulfate, and evaporated to give 650 mg of a residue, which is recrystallized from dichloromethane-petroleum ether to give 535 mg of 2-carboxy-5-thenoyl-7,8-dichloro-1,4-benzodioxine. (Ib''-2). Yield 77.8%, mp. 233°–236° C.

Anal. Calcd. (%) for $C_{14}H_6O_5Cl_2S$ (MW. 357.167): C 47.08, H 1.69, Cl 19.85, S 8.98, Found (%): C 46.92, H 1.95, Cl 19.85, S 8.79.

IR(Nujol) $\nu$max: 3120, 1718, 1660, 1590, 1565 cm$^{-1}$.

NMR(d$_6$-acetone) $\delta$ppm: 8.03(1H, d, d, J=6.2), 7.77(1H, d, d, J=6.2), 7.25(1H, d, d, J=6), 7.27(1H, s), 7.10(1H, s), 7.00–6.37(1H, b).

General Method

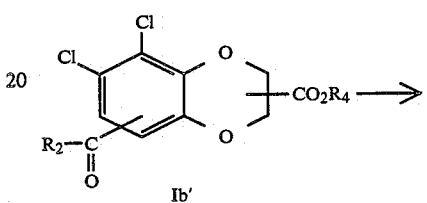

Ib'

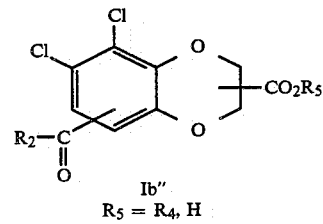

Ib''
$R_5 = R_4$, H

A solution of 1.5 g of a compound (Ib'), about 3.5 equimole of N-bromosuccinimide, and 200–250 mg of benzoyl peroxide dissoved in 80 ml of dry carbon tetrachloride is heated for 20 hours. After removal of the precipitate by the filtration, the filtrate is evaporated under reduced pressure to give a residue, to which, 3 g of sodium iodide and 100 ml of acetone is added. The mixture is refluxed for about 1–2 hours, and then worked up in a usual manner (washed with sodium thiosulfate to remove Br$_2$) to give a compound (Ib'') ($R_5$=$R_4$). To a solution of the compound in tetrahydrofuran or dioxane is added an aqueous solution of sodium hydroxide. The mixture is heated on a bath at 70° C. for 5 to 10 minutes, then allowed to stand for an hour, neutralized with hydrochloric acid and poured into water. Treatment in a conventional manner gives a compound Ib'' ($R_5$=H). Compounds prepared in the same manner as above and their physical constants are shown in Table 9.

TABLE 9

| Compd. I a-b' | Position of —COR$_2$ | Position of —COOR$_4$ | R$_2$ | R$_4$ | mp. °C. | Elementary Anal. C; Calcd. (%), F; Found (%) | IR(cm$^{-1}$) NMR($\delta$, Hz) |
|---|---|---|---|---|---|---|---|
| 3 | 5 | 2 | phenyl | Et | 153~155 | $C_{16}H_{12}O_5Cl_2$(Mw 379, 200)<br>C  H  Cl<br>C; 57.02  3.19  18.70<br>F; 56.51  3.33  19.56 | IR$\nu$max(Nujol) 1735, 1685, 1659<br>NMR(d$_6$-acetone) 7.97~7.44(5H),<br>7.24, 7.02(2 × 1H,s),<br>4.24(2H, q, J = 7), 1.26(3H, t, J = 7) |
| 4 | 5 | 2 | phenyl | H | 265~268 | $C_{16}H_8O_5Cl_2$(Mw 351, 145)<br>C  H  Cl<br>C; 54.73  2.30  20.19<br>F; 54.65  2.53  20.02 | IR$\nu$max(Nujol)<br>3500~2000(br), 1690, 1660<br>NMR(DMSO-d$_6$) 7.93~7.48(5H),<br>7.35, 7.17(2 × 1H,s) |
| 5 | 6 | 3 | o-fluorophenyl | Et | 169~171 | $C_{16}H_{11}O_5Cl_2F$(Mw 397, 185)<br>C  H  Cl  F<br>C; 54.43  2.79  17.85  4.78 | IR$\nu$max(Nujol) 1770, 1675, 1645,<br>1600, 1520<br>NMR(CDCl$_3$) 6.85, 7.02(2 × 1H,s), |

TABLE 9-continued

| Compd. I a-b' | Position of —COR₂ | Position of —COOR₄ | R₂ | R₄ | mp. °C. | Elementary Anal. C; Calcd. (%), F; Found (%) | IR(cm⁻¹) NMR($\delta$, Hz) |
|---|---|---|---|---|---|---|---|
| | | | | | | F; 54.14 2.90 17.75 4.82 | 7.83~6.83(4H,m), 4.27(2H, q, J = 7.0), 1.32(3H, t, J = 7.0) |
| 6 | 6 | 3 | o-fluorophenyl | H | 238~239 | $C_{16}H_7O_5Cl_2F$(Mw 369, 131)<br>C  H  Cl  F<br>C; 52.06 1.91 19.21 5.17<br>F; 51.96 2.24 19.51 5.22 | IR$\nu$max(Nujol) 1690, 1660, 1605, 1570<br>NMR(d₆-acetone) 6.97,<br>7.27(2 × 1H,s), 7.97~7.00(4H,m) |
| 7 | 6 | 3 | phenyl | Et | 155~157 | $C_{16}H_{12}O_5Cl_2$(Mw 379, 195)<br>C  H  Cl<br>C; 57.01 3.19 18.07<br>F; 57.22 3.26 18.59 | IR$\nu$max(Nujol) 1720, 1660, 1590, 1575<br>NMR(CDCl₃) 6.82,<br>7.07(2 × 1H,s), 7.90~7.30(5H,m), 4.30(2H, q, J = 7.0), 1.32(3H, t, J = 7.0) |
| 8 | 6 | 3 | phenyl | H | 250~252 | $C_{16}H_8O_5Cl_2$(Mw 351, 141)<br>C  H  Cl<br>C; 54.73 2.30 20.19<br>F; 54.39 2.53 19.96 | IR$\nu$max(Nujol) 1700, 1678, 1660, 1595, 1575<br>NMR(d⁶-DMSO) 7.07,<br>7.35(2 × 1H,s), 7.93~7.43(5H,m) |
| 9 | 6 | 3 | 2-thienyl | Et | 171~173 | $C_{16}H_{13}O_5Cl_2S$(Mw 385, 221)<br>C  H  Cl  S<br>C; 49.89 2.62 18.41 8.32<br>F; 49.69 2.74 18.38 8.13 | NMR(CDCl₃) 6.83, 7.02(2 × 1H,s), 7.05(1H, t, J = 4.0), 7.45(1H, dd, J = 4.0, 1.0), 7.77(1H, dd, J = 4.0, 1.0), 4.28(2H, q, J = 7.0), 1.32(3H, t, J = 7.0) |
| 10 | 6 | 3 | 2-thienyl | H | 281~283 | $C_{14}H_6O_5Cl_2S$(Mw 357, 167)<br>C  H  Cl  S<br>C; 47.08 1.69 19.85 8.98<br>F; 46.87 2.12 20.04 8.71 | IR$\nu$max(Nujol) 1700, 1660, 1642, 1600, 1570<br>NMR(d⁶-DMSO) 7.13,<br>7.37(2 × 1H,s), 7.30(1H, t, J = 5.0), 7.60(1H, dd, J = 5.0, 1.0), 8.17(1H, dd, J = 5.0, 1.0) |
| 11 | 6 | 2 | phenyl | Et | 95~96 | $C_{16}H_{12}O_5Cl_2$(Mw 379, 195)<br>C  H  Cl<br>C; 57.01 3.19 18.70<br>F; 56.41 3.26 19.00 | IR$\nu$max(Nujol) 1725, 1670, 1595, 1570<br>NMR(CDCl₃) 6.68(1H,s), 6.97(1H,s), 7.27~7.92(5H,m), 4.33(2H, q, J = 7.0), 1.33(3H, t, J = 7.0) |
| 12 | 6 | 2 | 2-thienyl | Et | 126~127 | $C_{16}H_{10}O_5Cl_2S$(Mw 385, 221)<br>C  H  Cl  S<br>C; 49.89 2.62 18.41 8.32<br>F; 49.86 2.92 18.45 8.23 | IR$\nu$max(Nujol) 1725, 1670, 1645, 1600, 1570<br>NMR(d₆-acetone)<br>1.30(3H, t, J = 7.0), 4.25(2H, q, J = 7.0), 7.00(1H,s), 7.20(1H,s), 7.23(1H, t, J = 5.0), 7.60(1H, dd, J = 5.01, 1.0), 8.03(1H, dd) |
| 13 | 6 | 2 | 2-thienyl | H | 274~276 | $C_{14}H_6O_5Cl_2S$(Mw 357, 167)<br>C  H  Cl  S<br>C; 47.08 1.69 19.85 8.98<br>F; 46.99 2.00 19.86 9.02 | IR$\nu$max(Nujol) 1705, 1670, 1640, 1570<br>NMR(d₆-acetone)<br>6.95, 7.17(2 × 1H,s), 7.18(1H, t, J = 0.5), 7.55(1H, dd, J = 5.0, 1.0), 7.98(1H, dd, J = 5.0, 1.0) |

EXAMPLE 5

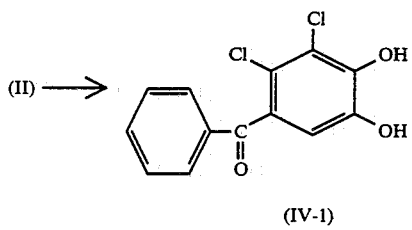

(II) →  (IV-1)

To a solution of 39.5 g (0.281 mol) of benzoyl chloride dissolved in 118 ml of dry dichloroethane is added 46.83 g (0.351 mol) of aluminium chloride. A solution of 15.712 g (0.088 mol) of the starting material (II) in dry dichloroethane (197 ml) is dropwise added to the mixture while being stirred for about 20 minutes and then the reaction mixture is refluxed for about 20 hours. After cooled, the mixture is poured into ice-water/conc. hydrochloric acid whereby the aluminium chloride is decomposed. The resulting mixture is extracted 3 times with ethyl ether and the organic layers are washed twice with a saturated solution of sodium chloride, dried over sodium sulfate, and evaporated under reduced pressure to give a residue (51.10 g).

A mixture of the residue, 210 ml of ethanol, and 210 ml of 2N-sodium hydroxide is refluxed for 30 minutes, evaporated under reduced pressure, neutralized by the addition of hydrochloric acid, and the resulting mixture is extracted twice with ethyl ether. The organic layers are washed with water, dried over sodium sulfate, and evaporated to dryness to give a residue, which is recrystallized from dichloromethane/petroleum ether to give 20.824 g (yield 83%) of the titled compound (IV-1), m.p. 178°–180° C.

Anal. Calcd. (%) for $C_{13}H_8Cl_2O_3$: C; 55.15, H; 2.85, Cl; 25.05, Found (%): C; 55.05; H; 2.98, Cl; 25.30.

IR(Nujol) $\nu$max: 3425, 3100, 1655, 1595, 1580 cm⁻¹.

NMR(d⁶-acetone) $\delta$ppm: 6.95 (1H, s), 7.93–7.50 (5H, m).

Process 1' (General Procedure):

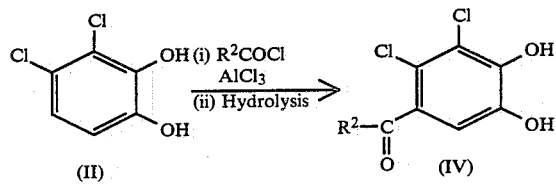

A mixture of the starting material (II) (0.01 mol), R²COCl (0.04-0.03 mol), and AlCl₃ (0.025-0.03 mol) in 350 ml of dichloroethane is refluxed for about 20 hours and poured into ice-water/conc. hydrochloric acid. The mixture is extracted with ethyl ether or ethyl acetate. The organic layer is combined with 250 ml of ethanol and 250 ml of 2N-sodium hydroxide, and the mixture is then refluxed for about 30 minutes to give a 5-acyl compound (IV). Thus prepared compounds and their physical constants are shown in Table 10.

dried over sodium sulfate, and evaporated to dryness to give a residue, which is chromatographed on silica gel with dichloromethane as an eluent. After removal of the solvent, the product is recrystallized from benzene to give 2.791 g (yield 71.4) of the captioned compound (V-b-2), m.p. 156°–157° C.

In the same manner as above, the compounds (V-b-1) and (V-b-3) listed in the following table are prepared, whose physical constants are shown in Table 11.

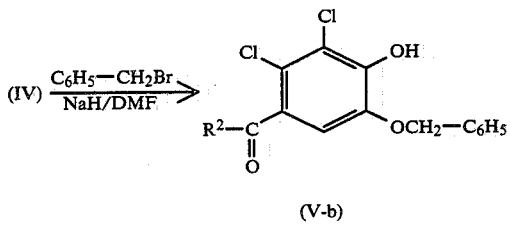

TABLE 11

| Compd. V-b | R₂ | Yield % mp. (°C.) | Elementary Analysis (%) | | | | IR(cm⁻¹) NMR |
|---|---|---|---|---|---|---|---|
| | | | | C | H | Cl | |
| 1 | phenyl | 77% 171~173° C. | C₂₀H₁₄O₂Cl₂ C; F; | 64.36 64.31 | 3.78 3.77 | 19.00 19.05 | IRνmax(Nujol) 3455, 1668, 1598, 1573 cm⁻¹ NMR(CDCl₃) 6.97(1H,s), 7.40(5H,s), 7.90~7.40(5H,m) |
| | | | | C | H | Cl | F |
| 2 | o-fluoro-phenyl | 71% 156~157° C. | C₂₀H₁₃O₃Cl₂F C; F; | 61.40 61.41 | 3.35 3.40 | 18.12 18.24 | 4.86 4.73 | IRνmax(Nujol) 3200, 1655, 1615 cm⁻¹ NMR(CDCl₃) 7.78~6.98(4H,m), ca. 7.41(5H), 7.07(1H,s), 6.34(1H,s), 5.12(2H,s) |
| 3 | 2-thienyl | 70% 146~148°C. | C₁₈H₁₂O₃Cl₂S C; F; | 57.00 56.87 | 3.19 3.30 | 18.70 18.56 | 8.45 8.44 | IRνmax(Nujol) 3450, 1648, 1600 cm⁻¹ NMR(CDCl₃) 7.73(1H, dd, J = 5,1), 7.32(1H, dd, J = 5,1), 7.08 (1H, t, J = 5), 7.38(5H,s), 6.95(1H,s), 6.40(1H,b), 5.13(2H,s) |

TABLE 10

| Compd. IV | R₂ | Yield % mp. (°C.) | Elementary Analysis (%) | | | | IR(cm⁻¹) NMR |
|---|---|---|---|---|---|---|---|
| | | | | C | H | Cl | F |
| 2 | o-fluoro-phenyl | 75% 164~165° C. | C₁₃H₇O₃Cl₂F C; F; | 51.86 51.88 | 2.34 2.47 | 23.55 23.49 | 6.31 6.28 | IRνmax(Nujol) 3400, 3170, 1665, 1655, 1610 cm⁻¹ NMR(CDCl₃) 9.50~8.40(2H,br), 7.78~7.10(4H,m), 7.03(1H,s) |
| 3 | 2-thienyl | 80% 202~204° C. | C₁₁H₆O₃Cl₂S C; F; | 45.69 45.48 | 2.09 2.38 | 24.53 24.60 | 11.09 11.09 | IRνmax(Nujol) 3360, 1720, 1710 cm⁻¹ NMR(d₆-acetone) 8.97(2H,br), 7.97(1H, dd, J = 5.1), 7.53(1H, dd, J = 5.1), 7.17(1H, t, J = 5), 6.97(1H,s) |

EXAMPLE 6

Process 2: Method B (Step 1):

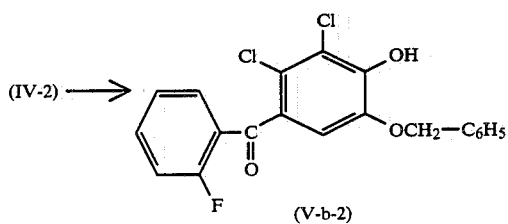

To a solution of 3.01 g (0.01 mol) of the starting material (IV-2) dissolved in 50 ml of DMF are added 480 g (0.02 mol) of sodium hydride and then 1.88 g (0.011 mol) of benzyl bromide, and the mixture is stirred for 15 minutes at room temperature. The reaction mixture is poured into ice-water, acidified by addition of diluted hydrochloric acid, and extracted with ethyl ether three times. The organic layer is washed twice with water,

EXAMPLE 7

Process 2: Method A (Step 1)

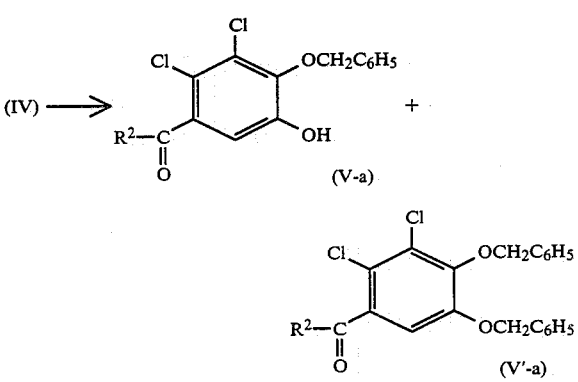

To a solution of 3.217 mg of the starting material (IV-2) in 90 ml of DMF is added a solution of sodium hydride (1.1 mol) and benzyl bromide (1.919 g, 1.05 mol) in DMF (10 ml), and the mixture is stirred at 100° C. for 2 hours, poured into ice-water, and acidified by addition of hydrochloric acid. The mixture is extracted with ethyl ether and the organic layer is washed with water and evaporated to dryness to give 4.124 g of a residue, which is then chromatographed on silica gel (SiO$_2$, 100 g) with dichloromethane as an eluent to give the compound (V'-a, 2) as the first fraction and the compound (V-a, 2) as the second fraction. The products are recrystallized from hexane to give 766 mg (yield 14.4%) of the compound (V'-a, 2), m.p. 84°–85° C. and 2.189 g (yield 52%) of the compound (V-a, 2), m.p. 109°–110° C., respectively.

In the same manner as above, the compounds (V-a, 1)($R^2$=o-phenyl) and (V-a, 3)($R^2$=2-thienyl) are prepared, whose physical constants are shown in Table 12.

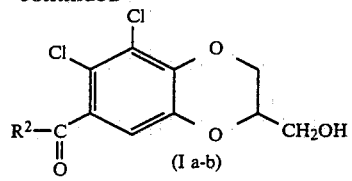

To a solution of 290 mg of 50% sodium hydride (washed out with petroleum ether) in DMF (40 ml) are added a solution of 1.570 g (4.13 mmol) of the compound (V-b, 3) ($R^2$=2-thienyl) dissolved in DMF (40 ml) and then a solution of 822 mg (6 mmol) of α-epibromohydrin in DMF (5 ml). The mixture is stirred under heating at a temperature of 75° to 80° C. for 5 hours. The reaction mixture is poured into ice-water and extracted with ethyl ether, and the organic layer is washed with water, dried over sodium sulfate, and evaporated to leave 1.570 g of a neutral fraction and 280 mg of an acidic fraction.

TABLE 12

| Compd. | R$_2$ | Yield % mp. (°C.) | Elementary Analysis (%) | | | | IR (cm$^{-1}$) NMR |
|---|---|---|---|---|---|---|---|
| V-a-1 | phenyl | 34% 111~112° C. | C$_{26}$H$_{14}$O$_3$Cl$_2$(Mw 373, 235) | | | | IRνmax(Nujol) 3350,1665,1655,1597,1580 |
| | | | C | H | Cl | | NMR(CDCl$_3$) 6.87(1H,s),7.45(5H,s),7.93~7.45(5H,m),5.73 |
| | | | C; 64.36 | 3.78 | 19.00 | | (1H,OH) |
| | | | F; 64.34 | 4.00 | 18.79 | | |
| V-a-2 | o-fluoro- phenyl | 52% 109~110° C. | C$_{20}$H$_{13}$O$_3$Cl$_2$S | | | | IRνmax(Nujol) 3210,1670,1610 |
| | | | C | H | Cl | F | NMR(CDCl$_3$) 7.86~7.00(4H,m),ca.7.45(5H),6.93(1H,s),5.64 |
| | | | C; 61.40 | 3.35 | 18.12 | 4.86 | (1H,s),5.14(2H,s) |
| | | | F; 61.41 | 3.50 | 18.34 | 4.81 | |
| V'a-2 | o-fluoro- phenyl | 14.4% 84~85° C. | C$_{27}$H$_{19}$O$_3$Cl$_2$S | | | | IRνmax(Nujol) 1645,1605NMR(CDCl$_3$) 7.83~6.99(4H,m),ca. |
| | | | C | H | Cl | F | 7.39(10H),7.04(1H,s),5.13(2H,s),5.10(2H,s) |
| | | | C; 67.37 | 3.98 | 14.73 | 3.95 | |
| | | | F; 67.28 | 3.95 | 14.61 | 3.90 | |
| V-a-3 | 2-thienyl | 39% 159~160° C. | C$_{18}$H$_{12}$O$_3$Cl$_2$S(Mw 379, 256) | | | | IRνmax(Nujol) 3300,1640,1581 |
| | | | C | H | Cl | F | NMR(CDCl$_3$) 7.78(H,dd,J = 5,1),7.42(1H,dd,J = 5,1),7.18 |
| | | | C; 57.00 | 3.19 | 18.70 | 8.45 | (1H,t,J = 5),7.43(5H,s),6.93(1H,s),5.68(1H,s),5.15(2H,s) |
| | | | F; 56.74 | 3.26 | 18.71 | 8.46 | |

EXAMPLE 8

Process 2': Method B (Step 2)

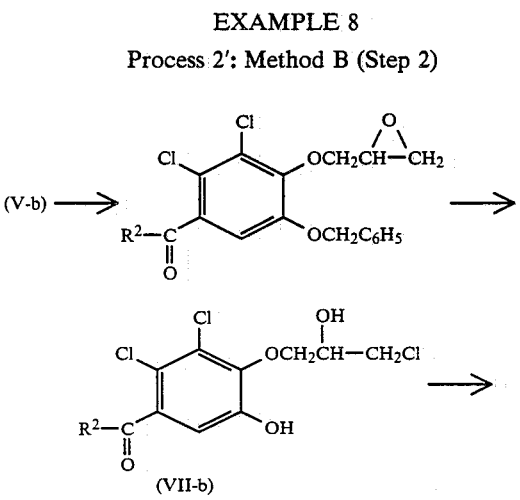

A mixture of 1.570 g of the neutral fraction with 100 ml of hydrochloric acid is refluxed for 10 hours and extracted with dichloromethane. The organic layer is washed with water and evaporated to dryness to give 1.500 g of a residue.

A mixture of the residue (1.500 g) with sodium hydroxide (500 mg) and ethanol (30 ml) is refluxed for 15 minutes and extracted with dichloromethane. The organic layer is washed with water and evaporated to give 1.350 g of a residual product, which is chromatographed on silica gel (8 g of silica gel, dichloroethane:ethyl ether=4:1) and then recrystallized from ethyl ether/petroleum ether to give 830 mg (yield 58%) of the captioned compound (Ia-b, 7), m.p. 137°–139° C. The physical constants of thus obtained compound was identical with those of the compound (Ia-b, 7) prepared in Example 2.

In the same manner as above, the objective compounds (Ia-b, 8) ($R^2$=phenyl), m.p. 201°–204° C. (yield 49%) and (Ia-b, 9) ($R^2$=o-fluorophenyl), m.p. 197°–199° C. (yield 59%) were prepared via the intermediates (VI-b, 1) and (VI-b, 2) shown in Table 13.

TABLE 13

| Compd. | R₂ | Yield % mp. (°C.) | Elementary Analysis (%) | IR (cm⁻¹) NMR |
|---|---|---|---|---|
| VI-b-2 |  (phenyl with F) | — 81~82° C. | $C_{23}H_{17}O_4Cl_2F$<br>C  H  Cl  F<br>C: 61.76  3.83  15.85  4.25<br>F: 61.64  4.01  15.79  4.15 | IR$_\nu$max(CHCl₃) 1665, 1607<br>NMR(CDCl₃) 7.83~7.07(4H,m), ca. 7.38(5H), 7.03(1H,s),<br>5.09(2H,s), 4.38~4.03(2H,m), 3.45~3.27(1H,m), 2.86~2.59 |
| VII-b-1 |  (phenyl) | — 83~84° C. | $C_{23}H_{18}O_4Cl_2$<br>C  H  Cl<br>C: 64.35  4.23  16.52<br>F: 64.14  4.34  16.53 | IR$_\nu$max(Nujol) 1660, 1600, 1980<br>NMR(d₆-acetone) 7.23(1H,s), 7.90~7.33(10,m), 5.27(2H,s),<br>4.55~3.92(2H,m), 3.47~3.17(1H,m), 2.83~2.50(2H,m) |

EXAMPLE 9

Process 2': Method A (Step 2)

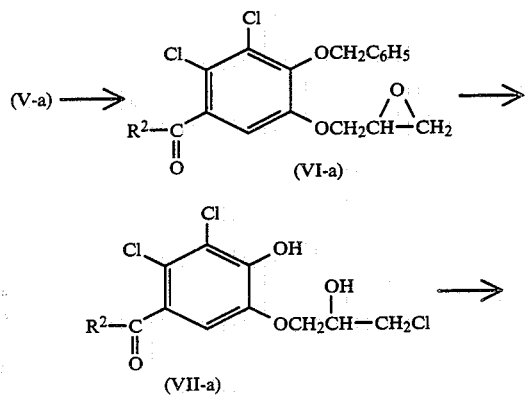

A solution of 2.300 mg (6.05 mmol) of the compound (Va, 3) (R²=2-thienyl) in 40 ml of DMF is added to a solution of 350 mg (7.26 mmol; washed out with petroleum ether) of 50% sodium hydride in 40 ml of DMF and the mixture is heated at 70°-80° C. for 5 hours. After cooled, the reaction mixture is poured into ice-water and extracted with ethyl ether. The organic layer is washed with water and evaporated to dryness to give 2.700 g of a residue as a neutral fraction.

A mixture of 2.700 g of the neutral fraction and 140 ml of hydrochloric acid is refluxed for 5 hours and extracted with ethyl acetate. The organic layer is washed with a saturated aqueous solution of sodium chloride and evaporated to give 2.300 g of a crystalline residue (VII-a, 3), m.p. 187°-189° C.

A mixture of 2.300 g of the residue with sodium hydride (700 mg) and ethanol (40 ml) is refluxed for 20 minutes and extracted with dichloromethane. The organic layer is washed with water and evaporated to dryness to give 1.900 g of a residue, which is chromatographed on silica gel. The benzene/dichloromethane fraction is recrystallized from ethyl acetate to give 1.317 g (yield 63%) of the compound (Ia-a, 6), m.p. 113°-114° C.

The physical constants of this product were identical with those of the compound prepared in Example 1.

In the same manner as above, the compound (Ia-a 28) (R²=o-fluorophenyl), m.p. 109°-110° C. (yield 45%) is prepared, whose physical constants were identical with those of the compound (Ia-a 28) prepared in Example 1.

Physical constants of the intermediates are shown in Table 14.

TABLE 14

| Compd. | R₂ | Yield % mp. (°C.) | Elementary Analysis (%) | IR (cm⁻¹) NMR |
|---|---|---|---|---|
| VI-a-2 |  (fluorophenyl) | — oil | — | IR$_\nu$max(CHCl₃) 1665, 1610<br>NMR(CDCl₃) 7.84~7.08(9H,m), 6.99(1H,s), 5.26(2H,s),<br>4.38~3.85(2H,m), ca. 3.35(1H), 2.93~2.67(2H,m) |
| VII-a-2 | " | — 144~146° C. | $C_{16}H_{12}O_4Cl_3F$(Mw 393, 629)<br>C  H  Cl  F<br>C: 48.82  3.07  27.02  4.83<br>F: 48.46  3.16  26.80  4.86 | IR$_\nu$max(Nujol) 3470, 3230, 1630, 1603<br>NMR(d₆-acetone) 7.81~7.11(4H,m), 7.23(1H,s), 7.5~6.2(2H, br), 4.33~4.14(1H,m), ca. 4.24(2H), ca. 3.81(2H) |

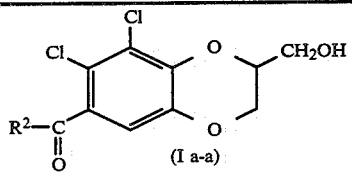

EXAMPLE 10

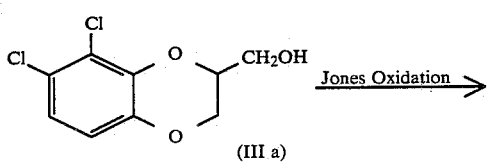

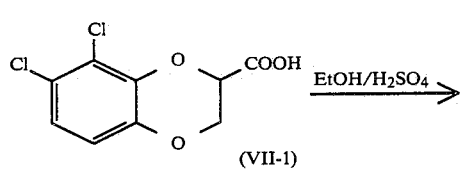

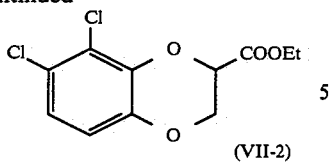

To a solution of 2.00 g of the starting material (IIIa) dissolved in 50 ml of acetone is dropwise added 5 ml of Jones' reagent (8N-$CrO_3$/$H_2SO_4$) over about 2 hours and methanol is then added thereto to kill the excess amount of chromic acid. After removal of the precipitate by filtration, the filtrate is evaporated under reduced pressure and extracted twice with ether. The organic layer is washed twice with a saturated aqueous solution of sodium chloride, dried over sodium sulfate, and evaporated to give 1.94 g of a residue, which is then recrystallized from dichloromethane/n-hexane to give 1.104 g (yield 52.1%) of 7,8-dichloro-1,4-benzodioxane-2-carboxylic acid (VIII-1), m.p. 144°–148° C.

A mixture of 8.294 g of the compound (VIII-1) with dry ethanol (200 ml) and concentrated sulfuric acid (0.5 ml) is stirred for 5 hours under an anhydrous condition and extracted with dichloromethane 3 times. The organic layer is washed with water, a saturated sodium hydrogencarbonate solution, and two portions of water, dried over sodium sulfate, and evaporated to give 9.051 g of a residue, which is recrystallized from dichloromethane/petroleum ether to give 8.75 g (yield 94.8%) of ethyl 7,8-dichloro-1,4-benzodioxane-2-carboxylate (VIII-2), m.p. 92°–94° C.

In the same manner as above, the following compounds were prepared, whose physical constants are shown in Table 15.

A mixture of 2.00 g of the compound (VIII-2) obtained in Example 10 with α,α-dichloromethyl methyl ether (12 ml) and dichloromethane (40 ml) is cooled on an ice-bath and 4.284 g of aluminium chloride is added thereto over about 20 minutes. The reaction mixture is stirred at room temperature for 3 hours. After confirming completion of the reaction by TLC, the reaction mixture is poured into ice-water/concentrated hydrochloric acid and extracted with dichloromethane 3 times. The organic layer is washed twice with a saturated aqueous solution of sodium chloride, dried over sodium sulfate, and evaporated to give 2.242 g of a residue.

This is passed through Lober column B (made by Merck) with benzene/acetone (30/1) as an eluent. The product in the earliest fraction is recrystallized from acetone/ether/petroleum ether to give 1.031 g (yield 47%) of the objective ethyl 6-formyl-7,8-dichloro-1,4-benzodioxane-2-carboxylate (Ib'-51), m.p. 101°–102° C. And the product in the later fractions are also recrystallized in the same manner as above to give 1.057 g (yield 49%) of ethyl 5-formyl-7,8-dichloro-1,4-benzodioxane-2-carboxylate (Ib'-50), m.p. 110°–113° C.

Titanium tetrachloride was employed in place of aluminium chloride, and the reaction was carried out in the same manner as above to give the compounds (Ib'-50) in 19% yield and (Ib'-51) in 39% yield.

In the same manner as above, the following compounds were prepared, whose physical constants are shown in Table 16.

TABLE 15

| Compd. VIII | S.M.* | Substituent and its position | m.p. °C. | Elementary Analysis (%) | IR (cm$^{-1}$) NMR |
|---|---|---|---|---|---|
| 1 | IIIa | —COOH (2) | 159~161 | $C_9H_6Cl_2O_4$(Mw 249, 049)<br>C H Cl<br>C; 43.40 2.43 28.47<br>F; 43.20 2.55 28.57 | IRνmax(Nujol) 3040,1747,1600,1580<br>NMR($d_6$-acetone) 7.88(1H,b),7.02,6.80(each 1H,d,J = 9),5.20<br>(1H,t,J = 3),4.70~4.23(2H,m) |
| 2 | IIIa | —COOEt (2) | 85~88 | $C_{11}H_{19}O_4Cl_2$(Mw, 277, 103)<br>C H Cl F<br>C; 47.68 3.64 25.59<br>F; 47.54 3.72 25.71 | IRνmax(Nujol) 1742,1600,1580<br>NMR(CDCl$_3$) 7.00,6.72( 1H,d,J = 8),4.98(1H,t,J = 8),4.67~<br>4.17(2H,m),4.27(2H,q,J = 8),1.27(3H,t,J = 8) |
| 3 | IIIb | —COOH (3) | 186~188 | $C_9H_6O_4Cl_2$(Mw 249, 052)<br>C H Cl<br>C; 43.40 2.43 28.47<br>F; 43.89 2.86 27.36 | IRνmax(Nujol) 3600~2200(br),1730<br>NMR($d_6$-acetone) 7.06,6.90(2 × 1H,d,J = 9),5.08(1H,t,J =<br>3),4.66,4.42(2 × 1H,dd,J = 3.13),9.5~8.0(1H,br) |
| 4 | IIIb | —COOEt (3) | 82~83 | $C_{11}H_{10}O_4Cl_2$(Mw 277, 107)<br>C H Cl<br>C; 47.68 3.64 25.59<br>F; 47.46 3.64 25.49 | IRνmax(Nujol) 1770,1750,1583NMR(CDCl$_3$) 7.03,6.86(2 × 1H<br>d,J = 9),4.82(1H,d,J = 4),ca.4.47(2H),4.26(2H,q,J = 7),1.26<br>(3H,t,J = 7) |

Note
*starting material

EXAMPLE 11

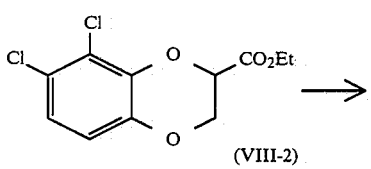

TABLE 16

![structure with Cl, Cl, CHO, O, R1, O on benzodioxane]

| Compd. Ia-a or Ib' | position of formyl | R' | m.p. °C. | Elementary Analysis (%) | IR (cm⁻¹) NMR |
|---|---|---|---|---|---|
| Ia-a-39 | 5 | —CH$_2$OAc | 142~144 | C$_{12}$H$_{19}$O$_6$Cl$_2$(Mw305, 113)<br>　　C　　H　　Cl<br>C; 47.24　3.30　23.24<br>F; 47.06　3.26　22.99 | IRνmax(Nujol) 1758,1678,1580<br>NMR(d$_6$-acetone) 10.25(1H,s),7.40(1H,s),<br>4.73~4.17(5H,m),2.07(3H,s) |
| Ia-a-40 | 6 | —CH$_2$OAc | 90~92 | C$_{12}$H$_{19}$O$_6$Cl$_2$(Mw305, 113)<br>　　C　　H　　Cl<br>C; 47.24　3.30　23.24<br>F; 47.25　3.23　23.30 | IRνmax(Nujol) 1732,1578,1590,1558<br>NMR(d$_6$-acetone) 10.23(1H,s),7.33(1H,s),<br>4.73~4.07(3H,m),2.07(3H,s) |
| Ia-a-41 | 5 | —CH$_2$OH | 99~100 | C$_{10}$H$_8$O$_4$Cl$_2$(Mw263, 076)<br>　　C　　H　　Cl<br>C; 45.66　3.07　26.95<br>F; 45.58　3.19　26.67 | IRνmax(Nujol) 3440,1680,1585<br>NMR(d$_6$-acetone) 10.30(1H,s),7.40(1H,s),<br>4.77~4.25(3H,m),4.07~3.87(2H,broad) |
| Ia-a-42 | 6 | —CH$_2$OH | 127–128 | C$_{10}$H$_8$O$_4$Cl$_2$(Mw263, 076)<br>　　C　　H　　Cl<br>C; 45.66　3.07　26.95<br>F; 45.40　3.20　26.89 | IRνmax(Nujol) 3450,1690~1670,1591,1560<br>NMR(d$_6$-acetone) 10.30(1H,s),7.33(1H,s),<br>4.70~4.17(3H,m),4.07~3.83(2H,b) |
| Ib'-50 | 5 | —COOEt | 110~113 | C$_{12}$H$_{10}$O$_6$Cl$_2$(Mw305, 113)<br>　　C　　H　　Cl<br>C; 47.24　3.30　23.24<br>F; 47.11　3.41　22.90 | IRνmax(Nujol) 3080,1755,1690,1588,1575<br>NMR(d$_6$-acetone) 10.20(1H,s),7.40(1H,s),<br>5.37(1H,t,J = 2),4.73~4.40(2H,m),4.27(2H,<br>q,J = 8),1.25(3H,t,J = 8) |
| Ib'-51 | 6 | —COOEt | 101~102 | C$_{12}$H$_{10}$O$_6$Cl$_2$(Mw305, 113)<br>　　C　　H　　Cl<br>C; 47.24　3.30　23.24<br>F; 47.07　3.31　22.91 | IRνmax(Nujol) 3070,3040,1757,1690,1597,<br>1560<br>NMR(d$_6$-acetone) 10.33(1H,s),7.33(1H,s),<br>5.40(1H,t,J = 2),4.70~4.30(2H,m),4.25(2H,<br>q,J = 8),1.25(3H,t,J = 8) |
| Ib'-52 | 5 | —COOH | 254~257 | C$_{10}$H$_6$O$_6$Cl$_2$(Mw277, 059)<br>　　C　　H　　Cl<br>C; 43.35　2.18　25.59<br>F; 43.29　2.58　25.20 | IRνmax(Nujol) 1718,1683,1583<br>NMR(d$_6$-acetone) 9.27(1H,s),7.42(1H,s),<br>6.43(1H,b),5.36(1H,t,J = 3),4.90~4.47(2H,m) |
| Ib-20 | 6 | —COOH | 262~263 | C$_{10}$H$_5$O$_6$Cl$_2$(Mw277, 059)<br>　　C　　H　　Cl<br>C; 43.35　2.18　25.59<br>F; 43.07　2.36　25.53 | IRνmax(Nujol) 1755,1658,1593,1558<br>NMR(d$_6$-acetone) 10.33(1H,s),7.35(1H,s),<br>5.40(1H,t,J = 3),4.75~4.33(2H,m) |

EXAMPLE 12

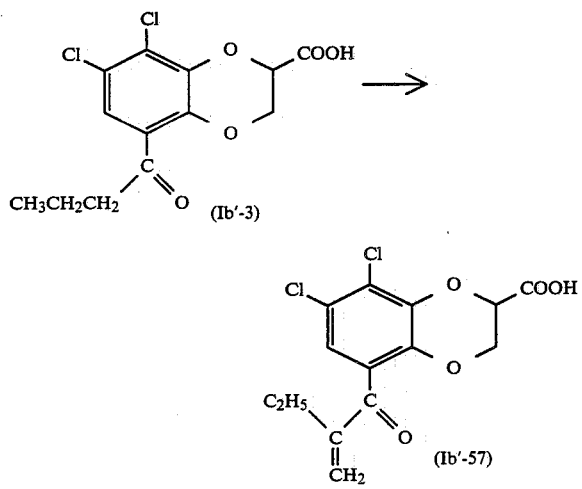

A solution of 1194 mg of the compound (Ib'-3), 449 mg (4 equiv.) of paraformaldehyde, and 710 mg of p-toluenesulfonic acid monohydrate dissolved in 15 ml of dioxane is stirred at 90° C. on an oil-bath for 27 hours. After completion of the reaction, the reaction mixture is concentrated and combined with benzene. The acidic portion of the mixture is moved into a saturated sodium hydrogencarbonate solution, made acidic with hydrochloric acid, and extracted with benzene 3 times. The organic layer is washed twice with water, dried over sodium sulfate, and evaporated to give 1474 mg of a residue, which is then chromatographed on 30 g of silica gel to give 748 mg of a product as the fraction of methylene chloride/ether (9/1). This is recrystallized from isopropyl ether/hexane to give 424 mg (m.p. 142°–143° C.) and 141 mg (m.p. 141°–143° C.) of the objective 2-carboxyl-5-(2-ethylacryloyl)-7,8-dichloro-1,4-benzodioxane (Ib'-57), total amount 565 mg, total yield 45.6%.

Anal. Calcd. (%) for C$_{14}$H$_{12}$O$_5$Cl$_2$ (molecular weight 331.15): C; 50.78, H; 3.65, Cl; 21.41. Found (%): C; 50.60, H; 3.82, Cl; 21.33.

IR(Nujol) νmax (cm⁻¹): 3500–2800(b), 1765, 1630.

NMR(d$_6$-acetone) δppm: 7.9–6.9(1H, b), 6.97(1H, s), about 5.91, 5.64(2×1H, s), 5.25(1H, t, J=3 Hz), 4.59, 4.37(2H×1H, d, d, J=3.13), 2.37(2H, q, J=7 Hz), 1.06(3H, t, J=7 Hz).

General Procedure

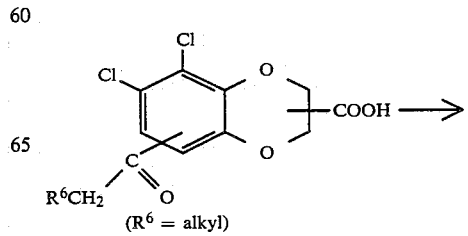

($R^6$ = alkyl)

-continued

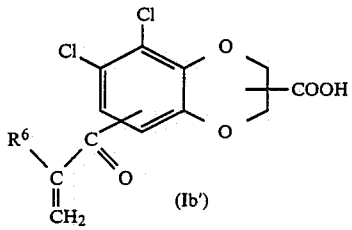

A solution of a starting material, paraformaldehyde, and p-toluenesulfonic acid dissolved in dioxane is refluxed for about 24 hours, and the resulting mixture is treated in a conventional manner to give an objective compound (Ib').

The starting material and physical constants on each compound obtained are shown in Table 17.

organic layer is washed with water and evaporated to give 1.004 g (93%) of 2-acetoxymethyl-7,8-dichloro-1,4-benzodioxane-5-carboxylic acid (Ia-a-43: $R^{3'}$=Ac), which is recrystallized from dichloromethane/ether to yield crystals, m.p. 144°–145° C.

Anal. Calcd. (%) for $C_{12}H_{10}O_6Cl_2$ (molecular weight 321.112): C; 44.89, H; 3.14, Cl; 22.08. Found (%): C; 44.62, H; 3.13, Cl; 21.67.

IR(Nujol) νmax (cm$^{-1}$): 2600, 1750, 1700, 1590, 1570.
NMR(CDCl$_3$) δppm: 7.68(1H, s), 4.87–4.17(5H, m), 2.10(3H, s).

To a solution of 1.00 g of the product (Ia-a-43) obtained above dissolved in a mixture of THF (30 ml) with ethanol (10 ml) is added an aqueous potassium carbonate solution (a solution of 2 g of potassium carbonate dissolved in 20 ml of water) and the resulting mixture is heated at 70°–80° C. for 5 minutes, then allowed to stand at room temperature for an hour. The mixture is made acid by addition of hydrochloric acid and ex-

TABLE 17

| Compd. Ib' | S.M. Ib' | Position of —CO$_2$H | Position of acyl | R$_6$ | m.p. °C. | Elementary Analysis (%) | IR (cm$^{-1}$) NMR (δ, Hz) |
|---|---|---|---|---|---|---|---|
| 58 | 1 | 2 | 5 | Me | 160~162 | $C_{13}H_{10}O_6Cl_2$(Mw 317, 128)<br>C  H  Cl<br>C; 49.24  3.18  22.36<br>F; 49.39  3.36  22.06 | IRνmax(Nujol) 3500~2300(br),1765, 1635,1622<br>NMR(d$_6$-acetone) 9.4~8.3(1H,br),<br>6.98(1H,s),ca.5.98(1H),5.64(1H,s),<br>5.26(1H,t,J = 3),4.59,4.35(2 × 1H,dd, J = 3,12)1.92(3H,d,J = 1.5) |
| 59 | 22 | 2 | 6 | Me | 155~158 | $C_{13}H_{10}Cl_2O_5$(Mw 317, 128)<br>C  H  Cl<br>C; 49.24  3.18  23.38<br>F; 49.35  3.46  21.82 | IRνmax(Nujol) 3200,1650,1600,1570<br>NMR(CDCl$_3$) 8.53(1H,s),6.76(1H,s),<br>5.99,5.54(2 × 1H,s),5.03(1H,t,J = 3),<br>4.63~4.22(2H,m),2.02(3H,s) |
| 60 | 23 | 2 | 6 | Et | 134~135 | $C_{14}H_{12}O_6Cl_2$(Mw 331, 155)<br>C  H  Cl<br>C; 50.78  3.65  21.41<br>F; 50.65  3.56  21.15 | IRνmax(Nujol) 3500~2800(br),1760, 1650<br>NMR(d$_6$-acetone) 8.0~6.3(1H,b),<br>6.83(1H,s),ca.600,5.60(2 × 1H),5.27<br>(1H,t,J = 3),2.66,4.42(2 × 1H,dd,J = 3.13),2.42(2H,q,J = 7),1.11(3H,t,J = 7) |
| 61 | 36 | 3 | 6 | Et | 187~189 | $C_{14}H_{12}O_6Cl_2$(Mw 331, 155)<br>C  H  Cl<br>C; 50.78  3.65  21.41<br>F; 50.66  3.60  21.49 | IRνmax(Nujol) 3600~2200(br),1710, 1650<br>NMR(d$_6$-acetone) 7.6~6.9(1H,br),<br>6.93(1H,s),6.01(1H,t,J = 1.5),5.63<br>(1H,s),5.16(1H,t,J =3),4.75,4.53(2 × 1H,dd,J = 3.13),2.43(2H,q,J = 7),1.12 (3H,t,J = 7) |

EXAMPLE 13

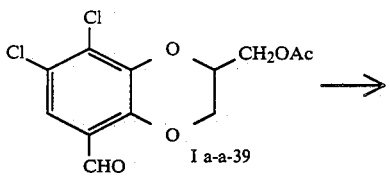

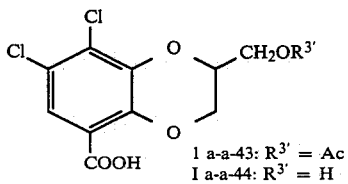

To a solution of 1.03 g of 2-acetoxymethyl-7,8-dichloro-1,4-benzodioxane-5-carbaldehyde (Ia-a-39) in 70 ml of acetone is added 2 ml of 8N-chromic acid/sulfric acid. The mixture is stirred at room temperature for about 2.5 hours and then filtered after the confirmation by TLC that no starting material is remained. The filtrate is concentrated under reduced pressure to give a residue, which is extracted with dichloromethane. The tracted with dichloromethane. The organic layer is washed with water, dried, and evaporated to give 980 mg of a residue, which is recrystallized from dichloromethane/ether to give 836 mg of 2-hydroxymethyl-7,8-dichloro-1,4-benzodioxane-5-carboxylic acid (Ia-a-44: $R^{3'}$=H), m.p. 175°–177° C.

Anal. Calcd. (%) for $C_{10}H_8O_5Cl_2$ (molecular weight 279.075): C; 43.04, H; 2.89, Cl; 25.41. Found (%): C; 42.80, H; 2.83, Cl; 25.65.

IR(Nujol) νmax (cm$^{-1}$): 3200, 1698–1705, 1585, 1565.
NMR(d$_6$-acetone) δppm: 7.58(1H, s), 4.70–4.20(3H, m), 3.93(2H, d, J=4.0).

According to the same reaction conditions as above, the following carboxylic acids were prepared from 2-acetoxymethyl-7,8-dichloro-1,4-benzodioxane-6-carbaldehyde (Ia-a-40).

*2-Acetoxymethyl-7,8-dichloro-1,4-benzodioxane-6-carboxylic acid, m.p. 178°–180° C. (from dichloromethane/ether).

Anal. Calcd. (%) for $C_{12}H_{10}O_6Cl_2$ (molecular weight 321.12): C; 44.89, H; 3.14, Cl; 22.08. Found (%): C; 44.61, H; 3.24, Cl; 22.34.

IR(Nujol) νmax (cm$^{-1}$): 3100, 1728, 1700, 1598, 1561.

NMR (d$_6$-acetone) δppm: 7.47(1H, s), 4.87–4.07(5H, m), 2.07(3H, s).

*2-Hydroxymethyl-7,8-dichloro-1,4-benzodioxane-6-carboxylic acid, m.p. 220°–221° C. (from acetone/ether).

Anal. Calcd. (%) for C$_{10}$H$_8$O$_5$Cl$_2$ (molecular weight 279.075): C; 43.04, H; 2.89, Cl; 25.41. Found (%): C; 42.77, H; 2.96, Cl; 25.43.

NMR(d$_6$-acetone) δppm: 7.40(1H, s), 4.67–4.13(3H, m), 3.90(2H, d, J=4).

The compounds (I) of the present invention have excellent antihypertensive and diuretic actions and are very useful for the treatment for hypertensives. They can be administered orally, intravenously, or hypodermically to human at a respective daily dosage of 0.1–2 mg/kg, 0.005–0.1 mg/kg, or 0.02–0.4 mg/kg. Diuretic effect and hyperuricosuric effect on the typical compounds are explained by the following Experiments.

EXPERIMENT 1

Estimation of Diuretic Effects

Test Method a. Diuretic Effect on Rats

Slc:SD 8-week-old rats (male, about 250 g bodyweight each) were used for the test. A few lumps of sugar in place of ordinary diets were given on the morning of the day before the test day and 5% glucose solution was given orally at a rate of 20 ml/kg in the evening (approximately at 4 p.m.) of the test day. In the morning for the test, a sample which was prepared by suspending or dissolving a test compound in 2% gum arabic was orally administered to each at a dose of 20 ml/kg. On the other hand, mere by 2% gum arabic was orally administered to the control group at 20 ml/kg. Immediately after the administration, the test animals were put in a plastic cage for the metabolic tests and their urine samples were collected for 5 hours. The cumulative urine volume, urinary sodium, and urinary potassium were quantitatively determined.

b. Diuretic Effect on Mice

Slc:ddy 5-week-old mice (female, about 20 g bodyweight each) were used for the test. From the morning of the day before the test day, the mice were fasted but water. In the morning of the test day, a sample which was prepared by suspending or dissolving a test compound in 2% gum arabic was orally administered to each at 30 ml/kg. On the other hand, mere by 2% gum arabic was orally administered to the control group at 30 ml/kg. Immediately after the administration, 5 mice employed were put in a plastic cage for the metabolic tests and their urine samples were collected for 4 hours. The cumulative urine volume, urinary sodium, and urinary potassium were quantitatively determined.

Results

Test results are shown in the following Table 1. Indacrinone (Merck Sharp & Dohme) was used as a reference.

TABLE 1

| | Experiment 1-a on Rats | | | | Experiment 1-b on Mice | | | |
|---|---|---|---|---|---|---|---|---|
| Compound | Dose mg/kg | Urine Vol.* ml/kg | Na$^{+*}$ mEg/kg | K$^{+*}$ mEg/kg | Dose mg/kg | Urine Vol.* ml/kg | Na$^{+*}$ mEg/kg | K$^{+*}$ mEg/kg |
| Ib'3 (Example 3) | 50 | 39.0/29.6 | 2.21/0.76 | 0.68/0.22 | 30 | 54.0/30.3 | 4.31/0.64 | 1.40/0.53 |
| Ib'1 (Example 3) | 50 | 50.8/32.6 | 3.04/0.71 | 0.86/0.25 | 30 | 54.5/25.9 | 5.68/0.78 | 1.41/0.55 |
| Ib'8 (Example 3) | 50 | 32.8/24.1 | 1.36/0.46 | 0.48/0.27 | 30 | 52.8/26.3 | 4.56/0.93 | 1.51/0.77 |
| Ib'4 (Example 3) | 50 | 38.8/23.5 | 3.54/0.75 | 1.42/0.42 | 30 | 60.2/24.7 | 5.78/0.82 | 1.68/0.57 |
| Ib'6 (Example 3) | 50 | 48.8/24.7 | 3.90/0.59 | 1.27/0.39 | 30 | 46.4/24.7 | 3.02/0.82 | 1.14/0.57 |
| Ib'41 (Example 3) | 50 | 30.1/28.3 | 1.49/0.54 | 0.58/0.25 | 30 | 29.0/22.1 | 1.08/0.58 | 0.88/0.57 |
| Ia-a1 (Example 1) | 50 | 36.6/32.5 | 1.62/0.71 | 0.47/0.25 | 30 | 33.7/25.9 | 2.39/0.78 | 0.86/0.55 |
| Ia-a3 (Example 1) | 50 | 40.0/32.6 | 1.93/0.71 | 0.48/0.25 | 30 | 23.2/22.1 | 1.09/0.58 | 0.68/0.57 |
| Referrence | 50 | 34.3/29.4 | 1.26/0.55 | 0.50/0.25 | 30 | 71.9/29.2 | 6.44/0.77 | 1.87/0.67 |

*Test Group/Control Group

EXPERIMENT 2

Estimation of Hyperuricosuric Effects

Test Method a. Experiment for Clearance

Slc:Wister 10-week-old male rats were used for the test. Potassium oxonate was intraperitoneally (hereinafter abbreviated as i.p.) administered to the test animals at a dose of 250 mg/kg in order to measure uric acid clearance and inulin clearance. Ninety minutes later, canulae were placed into the femoral artery, femoral vein, and urinary bladder and a tube for administration of drugs was placed into abdominal cavity on each animal under anesthesia with 50 mg/kg i.p. of pentobarbital.

Exact 2 hours after the first administration, potassium oxonate was administered again i.p. at a dose of 250 mg/kg and then 60% urethane (2 ml/kg) and 15% inulin (4 ml/kg) were subcutaneously injected. A mixture of 4% mannitol/1.5% inulin/0.9% saline was infused at a flow rate of 0.1 ml/min to the animal on a plate kept at 30° C. After the equilibrium for 40 minutes, arterial blood (0.2 ml each) samples were collected 6 times every 20 minutes, and five 20-minutes urines were collected. Immediately after the collection of every blood sample, the serum was separated therefrom, and the serum samples and the urine samples were stored in a refrigerator. A test compound was suspended in 1% gum arabic and the suspension was intraperitoneally administered at 2 ml/kg.

b. Measurement of Uric acid and Inulin

Uric acid in the serum or in the urine was quantitatively analyzed by the method of Yonetani et al's. [Y. Yonetani et al., *Japanese Journal of Pharmacology* 30, 829–840 (1980)]. Substantially by the fluorescence method of Vurek's and Pegram's using dimedone reagent [Vurek, G. G., Pegram, S. E., Anal. Biochem. 16, 409–419 (1966)], inulin was also quantitatively analyzed in the following manner. To 0.1 ml of diluted deprotenized-serum or urine employed for the measurement of uric acid was added 5 ml of 1% dimedone/phosphoric acid solution and the resulting mixture was heated for 5 minutes. The mixture was cooled in ice-cold water, combined with 2.0 ml of acetic acid, then shaken well, and the fluorescence was measured at 410 nm in the excitation wave length at 360 nm.

Test Results

In order to estimate hyperuricosuric effect on tienilic acid as a referrence, tienilic acid was administered to the animals at a dose of 100 mg i.p. and urine volume (ml/kg min.), urinary uric acid (ml/kg min.), and fractional excretion of uric acid [FEua (μg/ml): (Uric acid Clearance)/(Inulin Clearance)] were measured. In the tables, "zero" minute means the time when a drug was administered. A fraction before the administration and 4 fractions after the administration were employed for the measurement.

Results are shown in the following Table 2. Experiments with 1% gum arabic solution (2 ml/kg i.p.) were also made.

TABLE 2

| Time (minutes) | Urine Volume (ml/kg min.) | Urinary ua.*1 (ml/kg min.) | FE ua (μ g/ml) |
|---|---|---|---|
| a. 1% gum arabic at 2 ml/kg i.p. | | | |
| −20 to 0 | 0.32 | 0.166 | 0.650 |
| 0 to 20 | 0.30 | 0.182 | 0.660 |
| 20 to 40 | 0.29 | 0.191 | 0.654 |
| 40 to 60 | 0.29 | 0.159 | 0.566 |
| 60 to 80 | 0.27 | 0.170 | 0.581 |
| Increase (%)*2 | — | — | — |
| b. Tienilic acid at 100 mg/kg i.p. | | | |
| −20 to 0 | 0.31 | 0.176 | 0.648 |
| 0 to 20 | 0.35 | 0.212 | 0.634 |
| 20 to 40 | 0.37 | 0.296 | 0.694 |
| 40 to 60 | 0.33 | 0.329 | 0.740 |
| 60 to 80 | 0.30 | 0.359 | 0.744 |
| Increase (%)*2 | 9 | 70 | 8 |

NOTE:
*1"ua" means uric acid
*2Increase (%) = [(Mean value after administration) ÷ (value before administration) − 1] ×100

As indicated in the table, no significant increase in urine volume, urinary uric acid, and FE ua. was seen in the control group, while slightly positive diuretic effect and increase in urinary uric acid and FE ua. were observed in the Thienilic acid (at 100 mg/kg i.p.) group as references. In addition, no remarkable pharmacological activities concerning those test parameters were observed in the Tienilic acid (at 50 mg/kg i.p.) group.

Experiments on the compounds of this invention were made in the same manner as explained above and diuretic effect and hyperuricosuric effect were estimated. Increase (%) concerning each parameter on the typical compounds was shown in Table 3.

TABLE 3

| Test Compound | Dose (mg) i.p. | Increase (%) Urine Vol. | Increase (%) Urinary ua. | Increase (%) FE ua. |
|---|---|---|---|---|
| Tienilic acid | 50 | — | — | — |
| | 100 | 9 | 70 | 8 |
| I b'3 | 50 | 59 | 45 | 23 |
| I b'1 | 50 | 91 | 46 | 8 |
| I b'8 | 50 | — | 37 | 17 |
| I b'2 | 50 | 106 | 67 | 27 |

Conclusion

The compounds of the present invention are confirmed to be excellent diuretic antihypertensives having uricosuric activities from those experiments.

What we claim is:

1. A compound of the formula:

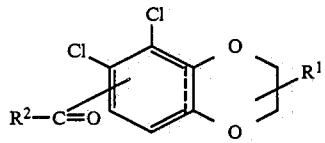

wherein $R^1$ is optionally protected hydroxymethyl or carboxy; $R^2$ is hydrogen, straight or branched chain lower alkyl or lower alkenyl, $C_4$–$C_7$ cycloalkyl, optionally substituted phenyl, phenyl(lower alkyl), hydroxy, thienyl, or furyl; and the dotted line indicates the presence or absence of a double bond.

2. A process for production of the compounds of the formula:

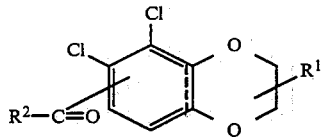

wherein $R^1$ is optionally protected hydroxymethyl or carboxy; $R^2$ is hydrogen, straight or branched chain lower alkyl or lower alkenyl, $C_4$–$C_7$ cycloalkyl, optionally substituted phenyl, phenyl(lower alkyl), hydroxy, thienyl, or furyl; and the dotted line indicates the presence or absence of a double bond, which is characterized by reaction of 3,4-dichloro-1,2-benzenediol of the formula:

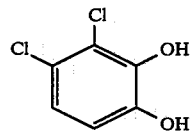

with α-epihalohydrin or the equivalent reagent thereof in the presence of a base followed by acylation in the presence of Lewis acid; or characterized by acylation of 3,4-dichloro-1,2-benzenediol in the presence of Lewis acid followed by reaction with α-epihalohydrin or the equivalent reagent thereof in the presence of a base, and if necessary, subsequent oxidation or dehydrogenation after the oxidation.

* * * * *